US008628750B2

(12) United States Patent
Wester et al.

(10) Patent No.: US 8,628,750 B2
(45) Date of Patent: *Jan. 14, 2014

(54) CANCER IMAGING AND TREATMENT

(75) Inventors: Hans Jürgen Wester, Ilmmünster (DE); Norman Koglin, Berlin (DE); Markus Schwaiger, München (DE); Horst Kessler, Garching (DE); Burkhardt Laufer, München (DE); Oliver Demmer, München (DE); Martina Anton, Vaterstetten (DE)

(73) Assignee: Technische Universitat Munchen, Hazelwood, MO (US)

( * ) Notice: Subject to any disclaimer, the term of this patent is extended or adjusted under 35 U.S.C. 154(b) by 845 days.

This patent is subject to a terminal disclaimer.

(21) Appl. No.: 12/280,829

(22) PCT Filed: Feb. 27, 2007

(86) PCT No.: PCT/GB2007/000684
§ 371 (c)(1),
(2), (4) Date: Oct. 14, 2010

(87) PCT Pub. No.: WO2007/096662
PCT Pub. Date: Aug. 30, 2007

(65) Prior Publication Data
US 2011/0027175 A1 Feb. 3, 2011

(30) Foreign Application Priority Data

Feb. 27, 2006 (GB) .................................. 0603901.0
Jun. 2, 2006 (GB) .................................. 0610962.3

(51) Int. Cl.
*A61K 51/00* (2006.01)
*A61M 36/14* (2006.01)

(52) U.S. Cl.
USPC ....... 424/1.69; 424/1.11; 424/1.65; 424/1.81; 424/1.85; 424/1.89; 424/9.1

(58) Field of Classification Search
USPC ........... 424/1.11, 1.65, 1.69, 1.81, 1.85, 1.89, 424/9.1, 9.3, 9.4, 9.5, 9.6, 9.7, 9.8; 514/1, 514/1.1; 534/7, 10–16; 530/300, 311, 317, 530/328

See application file for complete search history.

(56) References Cited

U.S. PATENT DOCUMENTS

| 5,869,447 A * | 2/1999 | Henke et al. ................ 424/278.1 |
| 2003/0194373 A1 | 10/2003 | Fauconnier et al. |
| 2004/0009149 A1 | 1/2004 | Altman et al. |

FOREIGN PATENT DOCUMENTS

| EP | 1 541 585 | 6/2005 |
| JP | 2004 196769 | 7/2004 |
| WO | WO 00/56729 | 9/2000 |
| WO | WO 01/37872 | 5/2001 |
| WO | WO 02/072631 | 9/2002 |
| WO | WO 03/066830 | 8/2003 |
| WO | WO 2004/087068 | 10/2004 |
| WO | WO 2004/092410 | 10/2004 |
| WO | WO 2004/094465 | 11/2004 |
| WO | WO 2005/058370 | 6/2005 |

OTHER PUBLICATIONS

Giblin, et al., "Radiometallation of Receptor-specific Peptides for Diagnosis and Treatment of Human Cancer", In Vivo. 2005, vol. 19, No. 1, pp. 9-29.
Fujii et al., "Molecular-size reduction of a potent CXCR4-chemokine antagonist using orthogonal combination of conformation- and sequence-based libraries", Angewandte Chemie, 2003, vol. 42, No. 28, pp. 3251-3253, XP002431585.
Fujii et al., "Preparation of cyclopeptides as chemokine receptor CXCR4 antagonists", retrieved from STN Database accession No. 141:123906, XP002460444.
Tamamura et al., "Identification of novel low molecular weight CXCR4 antagonists by structural tuning of cyclic tetrapeptide scaffolds", Journal of Medicinal Chemistry, 2005, vol. 48, No. 9, pp. 3280-3289, XP002460443.
Tamamura et al., "Structure-activity relationship studies on CXCR4 antagonists having cyclic pentapeptide scaffolds", Organic and Biomolecular chemistry, 2005, vol. 3, No. 24, pp. 4392-4394, XP009082932.
Houston et al., "Quality analysis of in vivo near-infrared fluorescence and conventional gamma images acquired using a dual-labeled tumor-targeting probe", Journal of Biomedical Optics, 2005, vol. 10, No. 5, pp. 54010-1, XP008061529.
Weiner et al., "Radiolabeled peptides in the diagnosis and therapy of oncological diseases", Applied Radiation and Isotopes, 2002, vol. 56, No. 5, pp. 749-763, XP004381731.
Liang et al., "Inhibition of breast cancer metastasis by selective synthetic polypeptide against CXCR4", Cancer Research, 2004, vol. 64, No. 12, pp. 4302-4308, XP002326726.
Haubner et al., "Radiolabeled alpha(v)beta3 integrin antagonists: a new class of tracers for tumor targeting", J. Nucl. Med., 1999, 40(6), pp. 1061-1071.
Gansbacher et al., "Retroviral vector-mediated gamma-interferon gene transfer into tumor cells generates potent and long lasting antitumor immunity", Cancer Res., 1990, 50(24), pp. 7820-7825.
Dubridge et al., "Analysis of mutation in human cells by using an Epstein-Barr virus shuttle system", Mol. Cell. Biol., 1987, 71(1), pp. 379-387.
Loetscher et al., "Cloning of a human seven-transmembrane domain receptor, LESTR, that is highly expressed in leukocytes", J. Biol. Chem., 1994, 269(1), pp. 232-237.

(Continued)

*Primary Examiner* — D L Jones

(57) ABSTRACT

Provided herein are compounds or conjugates useful for diagnostic imaging and/or therapeutic purposes. Each compound or conjugate comprises a ligand for the chemokine receptor CXCR4 and a detectable label. The ligand has a binding affinity for the CXCR4 receptor, measured as $IC_{50}$ in the presence of $^{125}I$-CPCR4, of 250 nM or lower, and the ligand comprises a cyclic oligopeptide moiety having the motif B-Arg or B-(Me)Arg within the cyclic moiety, wherein B is a basic amino acid, a derivative thereof, or phenylalanine, provided that the motif is B-Arg when B is a $N^\alpha$-methyl derivative of a basic amino acid.

19 Claims, 5 Drawing Sheets

(56) References Cited

OTHER PUBLICATIONS

Anton et al., Use of the norepinephrine transporter as a reporter gene for non-invasive imaging of genetically modified cells, J. Gene Med., 2004, 6(1), pp. 119-126.

Fan et al., "Hsc/Hsp 70 interacting protein (hip) associates with CXCR2 and regulates the receptor signaling and trafficking", J. Biol. Chem., 2002, 277(8), pp. 6590-6597.

Forester et al., "Intracellular and surface expression of the HIV-1 coreceptor CXCR4/fusion on various leukocyte subsets: rapid internalization and recycling upon activation", J. Immunol., 1998, 160(3), pp. 1522-1531.

Gupta et al., "Pharmacological evidence for complex and multiple site interaction of CXCR4 with SDF-1alpha: implications for development of selective CXCR4 antagonists", zimmunol. Zlryy., 3002, 78(1), pp. 29-34, (2002).

Hesselgesser et al., "Identification and characterization of the CXCR4 chemoline receptor in human T cell lines: ligand binding, biological activity, and HIV-1 infectivity", J. Immunol., 1998, 160(2), pp. 877-883.

Balkwill, "Cancer and the Chemokine Network", Nature Reviews, 2004, 4, pp. 540-550.

Fields et al., "Solid phase peptide synthesis utilizing 9-fluorenylmethoxycarbonyl amino acids", Int. J. Pept. Protein Res., 1990, 35, pp. 161-214.

Biron et al., "Optimized selective N-methylation of peptides on solid support", J. Peptide Sci., 2006, 12, pp. 213-219.

Müller et al., "Involvement of chemokine receptors in breast cancer metastasis", Nature, 2001, vol. 410, pp. 50-56.

Nagasawa et al., "Molecular cloning and structure of a pre-B-cell growth-stimulating factor", Proc. Natl. Acad. Sci., 1994, vol. 91, pp. 2305-2309.

Granero et al., Broad-Beam Transmission Data for New Brachytherapy Sources, Tm-17- and Yb-169.

Koglin et al., "Multimodal molecular imaging of CXCR4 chemokine receptor expression with peptide-based PET probes and bioluminescence", Abstract to the Society of Molecular Imaging: 5th Annual Meeting Hawaii, Sep. 2006.

AnorMED Inc., CXCR4 Chemokine Inhibitors in Oncology, www.anormed.com, Jul. 2006.

AnorMED Inc., Research & Development, "CXCR4 Inhibitors—Asthma, Rheumatoid Arthritis & Cancer", www.anormed.com.

Cabioglu et al., "Chemokine receptor CXCR4 expression in breast cancer as a potential predictive marker of isolated tumor cells in bone marrow", Clinical & Experimental Metastasis, 2005, 22, pp. 39-46.

Darash-Yahana et al., "Role of high expression levels of CXCR in tumor growth, vascularization, and metastasis", The FASEB Journal, FJ Express, vol. 18, Aug. 2004, pp. 12401242.

Saur et al., "CXCR4 Expression Increases liver and Lung Metastasis in a Mouse Model of Pancreatic Cancer", Gastroenterology, 2005, 1:29, pp. 1237-1250.

\* cited by examiner

Figure 2 Table A

| Comparison of $^{125}$I-CPCR4 binding parameters | | |
|---|---|---|
| | $K_D$ [nM] | $IC_{50}$ [nM] |
| Jurkat cell (endogenous receptor expression) | 0.4 (±0.1) | 4.0 (±0.2) |
| CMS5/CXCR4 cells | 0.3 (±0.1) | 6.5 (±0.8) |
| → Identical affinity and binding behavior of $^{125}$I-CPCR4 at both cell lines | | |
| → Application of transduced CMS5/CXCR4 cells as novel tumor model | | |

Figure 2 Table B

Affinity profile of CXCR4 selective ligands at Jurkat and CMS5/CXCR4 cells. $^{125}$I-CPCR4 and $^{125}$I-SDF-1α were used as radioligands, respectively. Affinity was expressed as $IC_{50}$ values in nM.

| | | CPCR4 | Iodo-CPCR4 | AMD3100 | SDF-1α |
|---|---|---|---|---|---|
| $^{125}$I-CPCR4 | Jurkat | 3.7 (±0.6) | (1): 0.01 (±0.01)<br>(2): 4.6 (±0.1) | 34.2 (±18.7) | (1): 0.12 (±0.1)<br>(2): 5.4 (±1.8) |
| $^{125}$I-CPCR4 | CMS5/CXCR4 | 6.8 (±0.8) | (1): 0.01 (±0.0)<br>(2): 3.5 (±0.2) | 51.5 (±29) | (1): 0.18 (±0.2)<br>(2): 21.7 (±3.3) |
| $^{125}$I-SDF-1α | CMS5/CXCR4 | (1): 0.01 (±0.01)<br>(2): 6.9 (±4.9) | (1): 0.02 (±0.01)<br>(2): 8.8 (±6.9) | n.d. | n.d. |

Figure 3 table

| Biodistribution analysis of ¹²⁵I-CPCR4 in tumor bearing nude mice [%ID/g] | | | |
|---|---|---|---|
| | 30min p.i. | 60min p.i. | 120min p.i. |
| Blood | 0.7 ±0.5 | 0.3 ±0.1 | 0.1 ±0.1 |
| Serum | 0.9 ±0.7 | 0.3 ±0.2 | 0.1 ±0.1 |
| Lung | 2.0 ±0.8 | 0.8 ±0.2 | 0.5 ±0.1 |
| Liver | 27.7 ±4.9 | 19.5 ±2.8 | 15.0 ±1.8 |
| Pancreas | 1.0 ±1.6 | 0.2 ±0.1 | 0.1 ±0.0 |
| Spleen | 1.9 ±0.5 | 1.0 ±0.3 | 0.7 ±0.1 |
| Intestine | 16.0 ±4.7 | 17.2 ±2.9 | 19.2 ±4.5 |
| Adrenals | 1.1 ±1.1 | 0.5 ±0.2 | 0.3 ±0.1 |
| Kidneys | 10.5 ±2.6 | 12.2 ±2.3 | 8.2 ±1.1 |
| Muscle | 0.2 ±0.1 | 0.1 ±0.0 | 0.0 ±0.0 |
| Bone | 0.4 ±0.1 | 0.2 ±0.0 | 0.1 ±0.0 |
| CXCR4-negative tumor | 1.0 ±0.3 | 0.6 ±0.2 | n.d. |
| CMS5/CXCR4-Tumor | 4.7 ±1.3 | 5.5 ±1.5 | 3.8 ±1.4 |

SEQUENCE LISTING

```
<160> NUMBER OF SEQ ID NOS: 105

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 1

Tyr Arg Arg Xaa Gly
1               5

<210> SEQ ID NO 2
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: methyl derivative of Arg
<220> FEATURE:
<221> NAME/KEY: MISC_FEATURE
<222> LOCATION: (4)..(4)
<223> OTHER INFORMATION: Xaa = L-3-(2-naphythyl)alanine

<400> SEQUENCE: 2

Tyr Arg Arg Xaa Gly
1               5

<210> SEQ ID NO 3
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: methyl derivative of Arg
<220> FEATURE:
<221> NAME/KEY: MISC_FEATURE
```

-continued

```
<222> LOCATION: (4)..(4)
<223> OTHER INFORMATION: Xaa = L-3-(2-naphthyl)alanine

<400> SEQUENCE: 3

Tyr Arg Arg Xaa Gly
1               5

<210> SEQ ID NO 4
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of Gly

<400> SEQUENCE: 4

Tyr Arg Arg Xaa Gly
1               5

<210> SEQ ID NO 5
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = ornithine
<220> FEATURE:
<221> NAME/KEY: MISC_FEATURE
<222> LOCATION: (4)..(4)
<223> OTHER INFORMATION: Xaa = L-3-(2_naphthyl)alanine

<400> SEQUENCE: 5

Tyr Xaa Arg Xaa Gly
1               5

<210> SEQ ID NO 6
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = citrulline
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 6

Tyr Xaa Arg Xaa Gly
1               5

<210> SEQ ID NO 7
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 7

Tyr Arg Arg Xaa Ala Gly
1               5
```

```
<210> SEQ ID NO 8
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 8

Tyr Arg Arg Xaa Ala Ala
1               5

<210> SEQ ID NO 9
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: methyl derivative of Arg
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of Gly

<400> SEQUENCE: 9

Tyr Arg Arg Xaa Gly
1               5

<210> SEQ ID NO 10
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: methyl derivative of Arg
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of L-3-(2-naphthyl)alanine

<400> SEQUENCE: 10

Tyr Arg Arg Xaa Gly
1               5

<210> SEQ ID NO 11
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Tyr
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 11

Tyr Arg Arg Xaa Ala Gly
1               5
```

-continued

```
<210> SEQ ID NO 12
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Tyr
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 12

Tyr Arg Arg Xaa Gly
1               5

<210> SEQ ID NO 13
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: fluorobenzoyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 13

Tyr Xaa Arg Xaa Gly
1               5

<210> SEQ ID NO 14
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: fluoropropionyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 14

Tyr Xaa Arg Xaa Gly
1               5

<210> SEQ ID NO 15
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: acetyl derivative of Ornithine
<220> FEATURE:
<221> NAME/KEY: MISC_FEATURE
```

```
<222> LOCATION: (4)..(4)
<223> OTHER INFORMATION: Xaa = L-3-(2-naphthyl)alanine

<400> SEQUENCE: 15

Tyr Xaa Arg Xaa Gly
1               5

<210> SEQ ID NO 16
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: amido derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 16

Tyr Xaa Arg Xaa Gly
1               5

<210> SEQ ID NO 17
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = 2,3-diaminopropionic acid
<220> FEATURE:
<221> NAME/KEY: MISC_FEATURE
<222> LOCATION: (5)..(5)
<223> OTHER INFORMATION: fluoropropionyl derivative of 2,3-
      diaminopropionic acid

<400> SEQUENCE: 17

Tyr Arg Arg Xaa Xaa
1               5

<210> SEQ ID NO 18
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: 1-naphthylmethyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 18

Tyr Xaa Arg Xaa Gly
1               5

<210> SEQ ID NO 19
```

-continued

```
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: 2-naphthylmethyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 19

Tyr Xaa Arg Xaa Gly
1               5

<210> SEQ ID NO 20
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: methyl and 1-naphthylmethyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 20

Tyr Xaa Arg Xaa Gly
1               5

<210> SEQ ID NO 21
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: methyl and 2-naphthylmethyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 21

Tyr Xaa Arg Xaa Gly
1               5

<210> SEQ ID NO 22
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
```

```
<222> LOCATION: (2)..(2)
<223> OTHER INFORMATION: methyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 22

Tyr Xaa Arg Xaa Gly
1               5

<210> SEQ ID NO 23
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: benzyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 23

Tyr Xaa Arg Xaa Gly
1               5

<210> SEQ ID NO 24
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: benzyl and fluorobenzoyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 24

Tyr Xaa Arg Xaa Gly
1               5

<210> SEQ ID NO 25
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: aminohexanoyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 25

Tyr Xaa Arg Xaa Gly
```

```
1               5

<210> SEQ ID NO 26
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: (aminohexanoyl)3 derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 26

Tyr Xaa Arg Xaa Gly
1               5

<210> SEQ ID NO 27
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: triethyleneglycolamino acyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 27

Tyr Xaa Arg Xaa Gly
1               5

<210> SEQ ID NO 28
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: (triethyleneglycolamino acyl)2 derivative of
      Ornithine
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 28

Tyr Xaa Arg Xaa Gly
1               5

<210> SEQ ID NO 29
<211> LENGTH: 5
<212> TYPE: PRT
<213> ORGANISM: Homo sapiens
<220> FEATURE:
<221> NAME/KEY: MISC_FEATURE
```

```
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: (triethyleneglycolamino acyl)3 derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 29

Tyr Xaa Arg Xaa Gly
1               5

<210> SEQ ID NO 30
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: methyl and fluorobenzoyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 30

Tyr Xaa Arg Xaa Gly
1               5

<210> SEQ ID NO 31
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: fluorobenzoyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 31

Tyr Xaa Arg Xaa Gly
1               5

<210> SEQ ID NO 32
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: methyl and fluorobenzoyl derivative of
      Ornithine
<220> FEATURE:
<221> NAME/KEY: MISC_FEATURE
```

```
<222> LOCATION: (4)..(4)
<223> OTHER INFORMATION: Xaa = L-3-(2-naphthyl)alanine

<400> SEQUENCE: 32

Tyr Xaa Arg Xaa Gly
1               5

<210> SEQ ID NO 33
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: methyl, fluorobenzoyl and methyl derivative of
      Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 33

Tyr Xaa Arg Xaa Gly
1               5

<210> SEQ ID NO 34
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 34

Tyr His Arg Xaa Gly
1               5

<210> SEQ ID NO 35
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 35

Tyr Phe Arg Xaa Gly
1               5

<210> SEQ ID NO 36
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: methyl derivative of D-Tyr
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 36

Tyr Tyr Arg Arg Xaa
1               5
```

```
<210> SEQ ID NO 37
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Ornithine
<220> FEATURE:
<221> NAME/KEY: MISC_FEATURE
<222> LOCATION: (2)..(2)
<223> OTHER INFORMATION: palmitoyl derivative of Ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 37

Tyr Xaa Arg Xaa Gly
1               5

<210> SEQ ID NO 38
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of L-3-(2-naphthyl)alanine

<400> SEQUENCE: 38

Tyr Arg Arg Xaa Gly
1               5

<210> SEQ ID NO 39
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of D-Tyr

<400> SEQUENCE: 39

Arg Xaa Gly Tyr Arg
1               5

<210> SEQ ID NO 40
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
```

```
<221> NAME/KEY: MISC_FEATURE
<222> LOCATION: (2)..(2)
<223> OTHER INFORMATION: methyl deriviatve of L-3-(2-naphthyl)alanine

<400> SEQUENCE: 40

Arg Xaa Gly Tyr Arg
1               5

<210> SEQ ID NO 41
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Gly
<220> FEATURE:
<221> NAME/KEY: MISC_FEATURE
<222> LOCATION: (4)..(4)
<223> OTHER INFORMATION: methyl derivative of D-Tyr

<400> SEQUENCE: 41

Arg Xaa Gly Tyr Arg
1               5

<210> SEQ ID NO 42
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of D-Tyr

<400> SEQUENCE: 42

Arg Xaa Gly Tyr Arg
1               5

<210> SEQ ID NO 43
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Gly
<220> FEATURE:
<221> NAME/KEY: MISC_FEATURE
<222> LOCATION: (5)..(5)
<223> OTHER INFORMATION: methyl derivative of Arg

<400> SEQUENCE: 43

Arg Xaa Gly Tyr Arg
1               5

<210> SEQ ID NO 44
```

```
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of D-Tyr
<220> FEATURE:
<221> NAME/KEY: MISC_FEATURE
<222> LOCATION: (5)..(5)
<223> OTHER INFORMATION: methyl derivative of Arg

<400> SEQUENCE: 44

Arg Xaa Gly Tyr Arg
1               5

<210> SEQ ID NO 45
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (3)..(3)
<223> OTHER INFORMATION: methyl derivative of Gly

<400> SEQUENCE: 45

Arg Xaa Gly Tyr Arg
1               5

<210> SEQ ID NO 46
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Gly

<400> SEQUENCE: 46

Arg Xaa Gly Tyr Arg
1               5

<210> SEQ ID NO 47
<211> LENGTH: 5
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
```

```
<220> FEATURE:
<221> NAME/KEY: MISC_FEATURE
<222> LOCATION: (5)..(5)
<223> OTHER INFORMATION: methyl derivative of Arg

<400> SEQUENCE: 47

Arg Xaa Gly Tyr Arg
1               5

<210> SEQ ID NO 48
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of Arg

<400> SEQUENCE: 48

Arg Xaa Gly Tyr Arg
1               5

<210> SEQ ID NO 49
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: Xaa = Ornithine
<220> FEATURE:
<221> NAME/KEY: MISC_FEATURE
<222> LOCATION: (5)..(5)
<223> OTHER INFORMATION: Xaa = Ornithine

<400> SEQUENCE: 49

Xaa Gly Tyr Xaa Xaa
1               5

<210> SEQ ID NO 50
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = ornithine

<400> SEQUENCE: 50

Xaa Gly Tyr Arg Xaa
1               5

<210> SEQ ID NO 51
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: Xaa = ornithine

<400> SEQUENCE: 51

Xaa Gly Tyr Xaa Arg
1               5

<210> SEQ ID NO 52
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: Xaa = citrulline
<220> FEATURE:
<221> NAME/KEY: MISC_FEATURE
<222> LOCATION: (5)..(5)
<223> OTHER INFORMATION: Xaa = citrulline

<400> SEQUENCE: 52

Xaa Gly Tyr Xaa Xaa
1               5

<210> SEQ ID NO 53
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: Xaa = citrulline

<400> SEQUENCE: 53

Xaa Gly Tyr Xaa Arg
1               5

<210> SEQ ID NO 54
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = citrulline

<400> SEQUENCE: 54

Xaa Gly Tyr Arg Xaa
1               5

<210> SEQ ID NO 55
<211> LENGTH: 5
<212> TYPE: PRT
<213> ORGANISM: Homo sapiens
```

```
<220> FEATURE:
<221> NAME/KEY: MISC_FEATURE
<222> LOCATION: (2)..(2)
<223> OTHER INFORMATION: Xaa = ornithine
<220> FEATURE:
<221> NAME/KEY: MISC_FEATURE
<222> LOCATION: (2)..(2)
<223> OTHER INFORMATION: (aminohexanoyl)2 derivative of ornithine
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 55

Tyr Xaa Arg Xaa Gly
1               5

<210> SEQ ID NO 56
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 56

Tyr Arg Arg Xaa Ala Gly
1               5

<210> SEQ ID NO 57
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Ala = D-Ala

<400> SEQUENCE: 57

Tyr Arg Arg Xaa Ala Gly
1               5

<210> SEQ ID NO 58
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = 2,3-diaminopropionic acid
<220> FEATURE:
<221> NAME/KEY: MISC_FEATURE
<222> LOCATION: (5)..(5)
<223> OTHER INFORMATION: fluoropropionyl derivative of 2,3-
      diaminopropionic acid

<400> SEQUENCE: 58

Tyr Arg Arg Xaa Xaa Gly
1               5

<210> SEQ ID NO 59
<211> LENGTH: 6
<212> TYPE: PRT
```

```
<213> ORGANISM: Homo sapiens
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 59

Tyr Arg Arg Ala Xaa Gly
1               5

<210> SEQ ID NO 60
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 60

Tyr Arg Arg Xaa Xaa Gly
1               5

<210> SEQ ID NO 61
<211> LENGTH: 6
<212> TYPE: PRT
<213> ORGANISM: Homo sapiens

<400> SEQUENCE: 61

Tyr Arg Arg Ala Ala Gly
1               5

<210> SEQ ID NO 62
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 62

Tyr Arg Arg Xaa Gly Gly
1               5

<210> SEQ ID NO 63
<211> LENGTH: 6
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 63

Tyr Arg Arg Ala Xaa Gly
1               5

<210> SEQ ID NO 64
<211> LENGTH: 6
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = L-3-(2-naphthyl)alanine
```

<400> SEQUENCE: 64

Tyr Arg Ala Arg Xaa Gly
1               5

<210> SEQ ID NO 65
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Ala = D-Ala
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 65

Tyr Arg Ala Arg Xaa Gly
1               5

<210> SEQ ID NO 66
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Ala = D-Ala
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 66

Tyr Ala Arg Arg Xaa Gly
1               5

<210> SEQ ID NO 67
<211> LENGTH: 6
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 67

Tyr Ala Arg Arg Xaa Gly
1               5

<210> SEQ ID NO 68
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Ala = D-Ala
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 68

Ala Thr Arg Arg Xaa Gly
1               5

<210> SEQ ID NO 69

```
<211> LENGTH: 6
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = L-3-(2-naphthyl)alanine

<400> SEQUENCE: 69

Ala Tyr Arg Arg Xaa Gly
1               5

<210> SEQ ID NO 70
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine

<400> SEQUENCE: 70

Tyr Arg Arg Xaa Ala Ala
1               5

<210> SEQ ID NO 71
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine

<400> SEQUENCE: 71

Arg Xaa Ala Gly Tyr Arg
1               5

<210> SEQ ID NO 72
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: Xaa = 2,3-diaminopropionic acid
<220> FEATURE:
<221> NAME/KEY: MISC_FEATURE
<222> LOCATION: (3)..(3)
<223> OTHER INFORMATION: fluoropropionyl derivative of 2,3-
      diaminopropionic acid

<400> SEQUENCE: 72

Arg Xaa Xaa Gly Tyr Arg
1               5

<210> SEQ ID NO 73
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
```

```
<400> SEQUENCE: 73

Arg Xaa Ala Gly Tyr Arg
1               5

<210> SEQ ID NO 74
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine

<400> SEQUENCE: 74

Arg Xaa Ala Gly Tyr Arg
1               5

<210> SEQ ID NO 75
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Ala

<400> SEQUENCE: 75

Arg Xaa Ala Gly Tyr Arg
1               5

<210> SEQ ID NO 76
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of Gly

<400> SEQUENCE: 76

Arg Xaa Ala Gly Tyr Arg
1               5

<210> SEQ ID NO 77
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of D-Tyr

<400> SEQUENCE: 77

Arg Xaa Ala Gly Tyr Arg
```

```
1               5

<210> SEQ ID NO 78
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (6)..(6)
<223> OTHER INFORMATION: methyl derivative of Arg

<400> SEQUENCE: 78

Arg Xaa Ala Gly Tyr Arg
1               5

<210> SEQ ID NO 79
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (6)..(6)
<223> OTHER INFORMATION: methyl derivaive of Arg

<400> SEQUENCE: 79

Arg Xaa Ala Gly Tyr Arg
1               5

<210> SEQ ID NO 80
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (6)..(6)
<223> OTHER INFORMATION: methyl derivative of Arg

<400> SEQUENCE: 80

Arg Xaa Ala Gly Tyr Arg
1               5

<210> SEQ ID NO 81
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
```

```
<220> FEATURE:
<221> NAME/KEY: MISC_FEATURE
<222> LOCATION: (6)..(6)
<223> OTHER INFORMATION: methyl derivative of Arg

<400> SEQUENCE: 81

Arg Xaa Ala Gly Tyr Arg
1               5

<210> SEQ ID NO 82
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Gly
<220> FEATURE:
<221> NAME/KEY: MISC_FEATURE
<222> LOCATION: (6)..(6)
<223> OTHER INFORMATION: methyl derivative of Arg

<400> SEQUENCE: 82

Arg Xaa Ala Gly Tyr Arg
1               5

<210> SEQ ID NO 83
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of D-Tyr
<220> FEATURE:
<221> NAME/KEY: MISC_FEATURE
<222> LOCATION: (6)..(6)
<223> OTHER INFORMATION: methyl derivative of Arg

<400> SEQUENCE: 83

Arg Xaa Ala Gly Tyr Arg
1               5

<210> SEQ ID NO 84
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: methyl derivative of D-Tyr

<400> SEQUENCE: 84

Arg Xaa Ala Gly Tyr Arg
1               5
```

-continued

```
<210> SEQ ID NO 85
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of D-Tyr

<400> SEQUENCE: 85

Arg Asn Ala Gly Tyr Arg
1               5

<210> SEQ ID NO 86
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (5)..(5)
<223> OTHER INFORMATION: methyl derivative of D-Tyr

<400> SEQUENCE: 86

Arg Xaa Ala Gly Tyr Arg
1               5

<210> SEQ ID NO 87
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (5)..(5)
<223> OTHER INFORMATION: methyl derivative of D-Tyr

<400> SEQUENCE: 87

Arg Xaa Ala Gly Tyr Arg
1               5

<210> SEQ ID NO 88
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
```

-continued

```
<223> OTHER INFORMATION: Xaa =  L-3-(2-naphthyl)alanine
<220> FEATURE:
<221> NAME/KEY: MISC_FEATURE
<222> LOCATION: (4)..(4)
<223> OTHER INFORMATION: methyl derivative of Gly

<400> SEQUENCE: 88

Arg Xaa Ala Gly Tyr Arg
1               5

<210> SEQ ID NO 89
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of Gly

<400> SEQUENCE: 89

Arg Xaa Ala Gly Tyr Arg
1               5

<210> SEQ ID NO 90
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (4)..(4)
<223> OTHER INFORMATION: methyl derivative of Gly

<400> SEQUENCE: 90

Arg Xaa Ala Gly Tyr Arg
1               5

<210> SEQ ID NO 91
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Ala

<400> SEQUENCE: 91

Arg Xaa Ala Gly Tyr Arg
1               5
```

```
<210> SEQ ID NO 92
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (3)..(3)
<223> OTHER INFORMATION: methyl derivative of Ala

<400> SEQUENCE: 92

Arg Xaa Ala Gly Tyr Arg
1               5

<210> SEQ ID NO 93
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine

<400> SEQUENCE: 93

Arg Xaa Ala Gly Tyr Arg
1               5

<210> SEQ ID NO 94
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (5)..(5)
<223> OTHER INFORMATION: methyl derivative of D-Tyr
<220> FEATURE:
<221> NAME/KEY: MISC_FEATURE
<222> LOCATION: (6)..(6)
<223> OTHER INFORMATION: methyl derivative of Arg

<400> SEQUENCE: 94

Arg Xaa Ala Gly Tyr Arg
1               5

<210> SEQ ID NO 95
<211> LENGTH: 6
<212> TYPE: PRT
<213> ORGANISM: Homo sapiens
<220> FEATURE:
<221> NAME/KEY: MISC_FEATURE
```

```
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (5)..(5)
<223> OTHER INFORMATION: methyl derivative of D-Tyr
<220> FEATURE:
<221> NAME/KEY: MISC_FEATURE
<222> LOCATION: (6)..(6)
<223> OTHER INFORMATION: methyl derivative of Arg

<400> SEQUENCE: 95

Arg Xaa Ala Gly Tyr Arg
1               5

<210> SEQ ID NO 96
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (6)..(6)
<223> OTHER INFORMATION: methyl derivative of Arg

<400> SEQUENCE: 96

Arg Xaa Ala Gly Tyr Arg
1               5

<210> SEQ ID NO 97
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (6)..(6)
<223> OTHER INFORMATION: methyl derivative of Arg

<400> SEQUENCE: 97

Arg Xaa Ala Gly Tyr Arg
1               5

<210> SEQ ID NO 98
<211> LENGTH: 6
<212> TYPE: PRT
<213> ORGANISM: Homo sapiens
<220> FEATURE:
```

```
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (6)..(6)
<223> OTHER INFORMATION: methyl derivative of Arg

<400> SEQUENCE: 98

Arg Xaa Ala Gly Tyr Arg
1               5

<210> SEQ ID NO 99
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (5)..(5)
<223> OTHER INFORMATION: methyl derivative of D-Tyr

<400> SEQUENCE: 99

Arg Xaa Ala Gly Tyr Arg
1               5

<210> SEQ ID NO 100
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (5)..(5)
<223> OTHER INFORMATION: methyl derivative of D-Tyr

<400> SEQUENCE: 100

Arg Xaa Ala Gly Tyr Arg
1               5

<210> SEQ ID NO 101
<211> LENGTH: 6
<212> TYPE: PRT
<213> ORGANISM: Homo sapiens
```

```
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (4)..(4)
<223> OTHER INFORMATION: methyl derivative of Gly
<220> FEATURE:
<221> NAME/KEY: MISC_FEATURE
<222> LOCATION: (5)..(5)
<223> OTHER INFORMATION: methyl derivative of D-Tyr

<400> SEQUENCE: 101

Arg Xaa Ala Gly Tyr Arg
1               5

<210> SEQ ID NO 102
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of  L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (5)..(5)
<223> OTHER INFORMATION: methyl derivative of D-Tyr

<400> SEQUENCE: 102

Arg Xaa Ala Gly Tyr Arg
1               5

<210> SEQ ID NO 103
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa =  L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (3)..(3)
<223> OTHER INFORMATION: methyl derivative of Ala
<220> FEATURE:
<221> NAME/KEY: MISC_FEATURE
<222> LOCATION: (4)..(4)
<223> OTHER INFORMATION: methyl derivative of Gly

<400> SEQUENCE: 103

Arg Xaa Ala Gly Tyr Arg
1               5

<210> SEQ ID NO 104
<211> LENGTH: 6
<212> TYPE: PRT
```

```
<213> ORGANISM: Homo sapiens
<220> FEATURE:
<221> NAME/KEY: MISC_FEATURE
<222> LOCATION: (1)..(1)
<223> OTHER INFORMATION: methyl derivative of Arg
<220> FEATURE:
<221> NAME/KEY: MISC_FEATURE
<222> LOCATION: (2)..(2)
<223> OTHER INFORMATION: Xaa = L-3-(2-naphthyl)alanine
<220> FEATURE:
<221> NAME/KEY: MISC_FEATURE
<222> LOCATION: (2)..(2)
<223> OTHER INFORMATION: methyl derivative of L-3-(2-naphthyl)alanine
<220> FEATURE:
<221> NAME/KEY: MISC_FEATURE
<222> LOCATION: (4)..(4)
<223> OTHER INFORMATION: methyl derivative of Gly

<400> SEQUENCE: 104

Arg Xaa Ala Gly Tyr Arg
1               5

<210> SEQ ID NO 105
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = L-3-(2-naphthyl)alanine
<220> FEATURE:
<221> NAME/KEY: MISC_FEATURE
<222> LOCATION: (5)..(5)
<223> OTHER INFORMATION: Xaa = 2,3-diaminopropionic acid
<220> FEATURE:
<221> NAME/KEY: MISC_FEATURE
<222> LOCATION: (5)..(5)
<223> OTHER INFORMATION: fluorobenzoyl derivative of 2,3-
    diaminopropionic acid

<400> SEQUENCE: 105

Tyr Arg Arg Xaa Xaa
1               5
```

CANCER IMAGING AND TREATMENT

CROSS REFERENCE TO RELATED APPLICATIONS

This application is a national stage application of PCT/GB2007/000684, filed Feb. 27, 2007, which claims the benefit of UK Application No. 0603901.0 filed Feb. 27, 2006 and UK Application No. 0610962.3 filed Jun. 2, 2006.

The present invention relates to the imaging and treatment of cancer. In particular, though not exclusively, it relates to compositions suitable for the targeting of radionuclides to cells expressing the chemokine receptor CXCR4 for the purposes of imaging and treatment thereof.

A method for the early assessment of the metastatic potential and metastatic spread of tumors would be a valuable tool for therapy prediction and control. Recently a key role in metastasis was attributed to the chemokine receptor CXCR4 (Müller et al. *Nature* 410 (2001) 50). In a variety of tumors such as breast and prostate cancer, CXCR4 has been found to play a dominating role during tumor cell homing and was shown to be expressed, both in primaries and metastases.

Stromal cell-derived factor 1α (SDF-1α) is the endogenous ligand for CXCR4 (Nagasawa T. et al. *PNAS.* 91 (1994) 2305). Peptide-based antagonists for CXCR4 have been described, including CPCR4 (also known as FC131, and having the sequence cyclo[D-Tyr-Arg-Arg-Nal-Gly]) (see Fujii N. et al., *Angew. Chem. Int. Ed* 42 (2003) 3251). CXCR4 is a co-receptor for HIV-1 and HIV-2, enabling entry of the viruses into cells. EP 1541585 describes radiolabeled SDF-1α for histology studies. This document also discloses a number of relatively bulky synthetic peptide antagonists of CXCR4. WO 2004/087608 discloses a CXCR4 antagonist labeled with biotin. Detection of such a compound requires the addition of a second, streptavidin-bearing reporter compound. The antagonists exemplified in WO 2004/087608 are peptides of 14 amino acids cyclised by means of a disulfide bond between Cys residues at positions 4 and 13. An Arg-Arg motif is present at positions 1 and 2, i.e. outside the cyclic moiety.

Until now, investigations with antagonists for CXCR4 (both peptide and non-peptide) have essentially been restricted to their potential use as inhibitors of the metastatic process or HIV infection.

Accordingly, a first aspect of the present invention provides a compound, or a pharmaceutically acceptable salt or ester thereof, comprising a ligand for the chemokine receptor CXCR4 and a detectable label, the ligand having a binding affinity for the CXCR4 receptor, measured as IC50 in the presence of $^{125}$I-CPCR4, of 250 nM or lower, wherein the ligand comprises a cyclic oligopeptide moiety having the motif B-Arg or B-(Me)Arg within the cyclic moiety, and wherein B is a basic amino acid, a derivative thereof, or phenylalanine, provided that the motif is B-Arg when B is a $N^\alpha$-methyl derivative of a basic amino acid.

In certain embodiments, the ligand for CXCR4 is preferably synthetic. It is currently preferred that the ligand binds to CXCR4 with an affinity (IC50) of 200 nM or less, more preferably 100 nM or less, and most preferably 50 nM or less. The term 'IC50' refers to the concentration of test compound required to reduce binding of the radiolabeled reference peptide $^{125}$I-CPCR4 to CXCR4-expressing cells to 50% of maximum binding. The person of ordinary skill in the art would readily be able to determine the IC50 of a given compound, and a method for doing so is described below. Compounds of the invention may bind to the CXCR4 receptor without activating the receptor (i.e. antagonist properties). Alternatively, compounds of the invention may compete with the endogenous ligand for the receptor, but activate the receptor to a lesser degree (i.e. partial agonist properties). As a further alternative, compounds of the invention may bind to the CXCR4 receptor and reduce subsequent signal transduction below the baseline, non-activated level (i.e. negative efficacy, or inverse agonist properties). In certain preferred embodiments, the compounds of the invention bind to the CXCR4 receptor without activating the receptor. In other preferred embodiments, the compounds of the invention do not comprise ligands with full agonist properties at CXCR4.

As used herein, the expression '(Me)Xaa' means an $N^\alpha$-methyl derivative of an amino acid. The expression 'Xaa (substituent)' means that the side chain of the amino acid is derivatised with the indicated substituent. The expression 'Xaa/(Me)Xaa' means that the stated amino acid may be unmethylated or may bear an $N^\alpha$-methyl group. The amino acid abbreviations used herein refer to the L-enantiomer of the respective amino acid, unless the expression 'D-Xaa' is used, in which case the D enantiomer is denoted. The term 'basic amino acid' as used herein denotes a naturally occurring or synthetic (preferably naturally occurring) amino acid having a side chain capable of receiving a proton, and becoming positively charged, under normal physiological conditions. Accordingly, basic amino acids include lysine, arginine, citrulline, ornithine, histidine, Dap (2,3-diaminopropionic acid) and Dab (2,4-diaminobutyric acid). Preferred basic amino acids are lysine, arginine, citrulline, ornithine and histidine, more preferably arginine and ornithine.

Compounds of the invention may provide an efficient probe for the in vivo targeting of the CXCR4 chemokine receptor. The compounds bind with high affinity and specificity to their binding site and allow ready imaging (by a variety of methods) and hence a clear delineation of CXCR4 positive tumors (and any associated metastases) in vivo. This new class of probes/tracers may provide highly valuable tools for the investigation of the metastatic potential of tumors and early imaging, and potentially radionuclide therapy, of metastatic processes The detectable label is preferably selected from fluorescent moieties, magnetic or paramagnetic moieties, or radionuclides. For many applications, radionuclides are preferred. The label is detectable without the addition of further reagents, by means of an output of detectable electromagnetic radiation or other nuclear radiation from the label itself, or as a result of its magnetic or paramagnetic properties. The ligand and the detectable label may be covalently bound to each other.

The cyclic oligopeptide moiety preferably comprises 20 amino acid residues or less, more preferably 9 residues or less. In preferred embodiments, the cyclic oligopeptide is a pentapeptide. The cyclic oligopeptide is preferably cyclised via a peptide bond, which may be between its N and C termini, or may be cyclised via a disulfide bond between two cysteine residues when present. The compound may include other moieties in addition to the cyclic oligopeptide moiety and the detectable label. Accordingly, additional peptide sequences may be attached, or groups capable of altering the pharmacokinetic and/or physicochemical properties of the compound (e.g. hydrophilic groups such as sugars or polyethylene glycol chains). The ligand may include additional components to the cyclic oligopeptide moiety. Alternatively, the ligand may consist of the cyclic oligopeptide moiety.

In certain preferred embodiments, the cyclic oligopeptide moiety has the sequence:

```
cyclo[D-Tyr/(Me)D-Tyr-B-Arg/(Me)Arg-Z-(Ala)_n-X]
``` wherein:

B is as defined above;

Z is an amino acid containing an aromatic group in its side chain;

n is 1 or 0, provided that n is 1 only when the preceding four amino acids in the cyclic moiety sequence are D-Tyr/(Me)D-Tyr-Arg-Arg-Nal, Nal being L-3-(2-naphthyl)alanine; and X⁻ is selected from Gly, (Me)Gly, Ala, Dap, Dap(FP) ((N-fluoropropionyl)-diaminopropionic acid), Dab, Dab (FP) ((N-fluoropropionyl)-diaminobutyric acid), Dab (FB) ((N-fluorobenzoyl)-diaminobutyric acid) and Dap (FB) ((N-fluorobenzoyl)-diaminopropionic acid).

Z may be selected from Nal, Dap(FB), AMS(FB) (an oxime of aminooxy serine (O-amino serine) and 4-fluorobenzaldehyde), and, when B is (Me)Arg, (Me)Nal. Z is preferably Nal.

X is preferably selected from Gly, (Me)Gly, Ala, Dap (diaminopropionic acid) and Dap(FP) ((N-fluoropropionyl)-diaminopropionic acid). X is preferably Gly or Dap(FP).

B is preferably a basic amino acid. The basic amino acid is preferably selected from Arg, Orn, D-Orn, Cit and His, or N-substituted derivatives thereof. Most preferably, B is Arg or Orn. Ornithine residues confer the advantage of an amino-containing side chain which is relatively straightforward to derivatise. In certain embodiments, B may be $N^\alpha$-substituted with a Me group. Preferably, no more than one residue in the cyclic oligopeptide moiety is $N^\alpha$-substituted with a Me group.

When B is Orn or D-Orn, the ornithine residue may be substituted at $N^\delta$ with one or two groups which may be selected from fluorobenzoyl (FB), fluoropropionyl (FP), acetyl (Ac), amido (Am) (i.e. so as to form a urea-type moiety), methyl (Me), 1-naphthylmethyl (N1), 2-naphthylmethyl (N2), benzyl (Bz) and acyl spacer moieties. Preferably, the acyl spacer moiety is an acyl group containing a chain of 1-14 carbons, optionally interrupted by heteroatoms, and preferably having a nucleophilic functional group at its end distal to the ornithine $N^\delta$. The nucleophilic functional group may be, for example, an amino or hydroxyl group. This group enables further moieties to be added to the end of the spacer, the purpose of the spacer being to minimise the effects of any additional groups on the CXCR4 binding capability of the cyclic oligopeptide. The acyl spacer moiety may be selected from aminohexanoyl (Ahx), triethyleneglycolamino acyl (TGAS, i.e. —$COCH_2(OCH_2CH_2)_2NH_2$), $(Ahx)_2$, $(Ahx)_3$, $(TGAS)_2$ and $(TGAS)_3$. When multimers of these spacers are present, the repeating units are joined together by amide bonds. Currently preferred spacer groups are Ahx, TGAS, $(Ahx)_3$, $(TGAS)_2$ and $(TGAS)_3$. The substituents described for ornithine, including the acyl spacer moieties, may also be employed when B is Lys, Dap or Dab. In such cases, the spacer moiety preferably has a nucleophilic functional group at its end distal to its point of attachment to the oligopeptide (i.e., the $N^\epsilon$ when B is Lys).

In certain embodiments, B is Orn or D-Orn, preferably D-Orn, substituted at $N^\alpha$ with a Me group. When B is Orn, it may be substituted at $N^\delta$ with FB, FP, Ac, Am, N1, N2, Me and N1, Me and N2, Bz, Bz and FB, Bz and FP, Me and FB, Me and FP, or Me.

In yet other embodiments, B is Orn or D-Orn, preferably D-Orn, substituted at $N^\delta$ with FB, FP, Me and FB, or Me and FP, and optionally substituted at $N^\alpha$ with a Me group. Preferred substituents in this instance are FB, and Me and FB, optionally in conjunction with substitution of $N^\alpha$ with a Me group.

The cyclic oligopeptide moiety may have the sequence: cyclo[D-Tyr-B-Arg-Z-X], wherein B, Z and X are selected from the options listed above, provided that not more than one of the residues in the said sequence may be $N^\alpha$-methylated. Preferably in such embodiments, B is Arg. Alternatively, the cyclic oligopeptide moiety may have the sequence: cyclo[D-Tyr/(Me)D-Tyr-B-Arg/(Me)Arg-Z-X], wherein Z and X are selected from the options listed above and wherein B is selected from Arg, (Me)Arg, Orn, Cit, Orn(FB), Orn(FP), Orn(Ac), Orn(Am), Orn(N1), Orn(N2), Orn(Me, N1), Orn (Me, N2), Orn(Me), Orn(Bz), Orn(Bz,FB), Orn(Ahx), Orn $(Ahx_2)$, Orn$(Ahx_3)$, Orn(TGAS), Orn$(TGAS_2)$, Orn $(TGAS_3)$, Orn(Me,FB), D-Orn(FB), (Me)D-Orn(FB), (Me)D-Orn(Me,FB), His and Phe, provided that not more than one of the residues in the said sequence may be $N^\alpha$-methylated. In such embodiments, the first residue is preferably D-Tyr. Also in such embodiments, Z is preferably Nal. Also in such embodiments, X is preferably Gly. Also in such embodiments, the third residue is preferably Arg.

In specific preferred embodiments, the cyclic oligopeptide moiety has a sequence selected from:

```
cyclo[D-Tyr-Arg-Arg-Nal-Gly]

cyclo[D-Tyr-(Me)Arg-Arg-Nal-Gly]

cyclo[D-Tyr-Arg-(Me)Arg-Nal-Gly]

cyclo[D-Tyr-Arg-Arg-Nal-(Me)Gly]

cyclo[D-Tyr-Orn-Arg-Nal-Gly]

cyclo[D-Tyr-Cit-Arg-Nal-Gly]

cyclo[D-Tyr-Arg-Arg-Nal-Ala-Gly]

cyclo[D-Tyr-Arg-Arg-Nal-Ala-Ala]

cyclo[D-Tyr-(Me)Arg-Arg-Nal-(Me)Gly]

cyclo[D-Tyr-(Me)Arg-Arg-(Me)Nal-Gly]

cyclo[(Me)D-Tyr-Arg-Arg-Nal-Ala-Gly]

cyclo[(Me)D-Tyr-Arg-Arg-Nal-Gly]

cyclo[D-Tyr-Orn(FB)-Arg-Nal-Gly]

cyclo[D-Tyr-Orn(FP)-Arg-Nal-Gly]

cyclo[D-Tyr-Orn(Ac)-Arg-Nal-Gly]

cyclo[D-Tyr-Orn(Am)-Arg-Nal-Gly]

cyclo[D-Tyr-Arg-Arg-Nal-Dap(FP)]

cyclo[D-Tyr-Orn(N1)-Arg-Nal-Gly]

cyclo[D-Tyr-Orn(N2)-Arg-Nal-Gly]

cyclo[D-Tyr-Orn(Me,N1)-Arg-Nal-Gly]

cyclo[D-Tyr-Orn(Me,N2)-Arg-Nal-Gly]

cyclo[D-Tyr-Orn(Me)-Arg-Nal-Gly]

cyclo[D-Tyr-Orn(Bz)-Arg-Nal-Gly]
```

```
    -continued
cyclo[D-Tyr-Orn(Bz,FB)-Arg-Nal-Gly]

cyclo[D-Tyr-Orn(Ahx)-Arg-Nal-Gly]

cyclo[D-Tyr-Orn(Ahx₃)-Arg-Nal-Gly]

cyclo[D-Tyr-Orn(TGAS)-Arg-Nal-Gly]

cyclo[D-Tyr-Orn(TGAS₂)-Arg-Nal-Gly]

cyclo[D-Tyr-Orn(TGAS₃)-Arg-Nal-Gly]

cyclo[D-Tyr-Orn(Me,FB)-Arg-Nal-Gly]

cyclo[D-Tyr-D-Orn(FB)-Arg-Nal-Gly]

cyclo[D-Tyr-(Me)D-Orn(FB)-Arg-Nal-Gly]

cyclo[D-Tyr-(Me)D-Orn(Me,FB)-Arg-Nal-Gly]

cyclo[D-Tyr-His-Arg-Nal-Gly]

cyclo[D-Tyr-Phe-Arg-Nal-Gly]
```

More preferred oligopeptide moieties include those having the following sequences

```
cyclo[D-Tyr-Arg-Arg-Nal-Gly]

cyclo[D-Tyr-(Me)Arg-Arg-Nal-Gly]

cyclo[D-Tyr-Arg-(Me)Arg-Nal-Gly]

cyclo[D-Tyr-Orn-Arg-Nal-Gly]

cyclo[D-Tyr-Cit-Arg-Nal-Gly]

cyclo[D-Tyr-Orn(FB)-Arg-Nal-Gly]

cyclo[D-Tyr-Orn(FP)-Arg-Nal-Gly]

cyclo[D-Tyr-Orn(Ac)-Arg-Nal-Gly]

cyclo[D-Tyr-Orn(Am)-Arg-Nal-Gly]

cyclo[D-Tyr-Orn(N1)-Arg-Nal-Gly]

cyclo[D-Tyr-Orn(N2)-Arg-Nal-Gly]

cyclo[D-Tyr-Orn(Me,N1)-Arg-Nal-Gly]

cyclo[D-Tyr-Orn(Me,N2)-Arg-Nal-Gly]

cyclo[D-Tyr-(Me)D-Orn(FB)-Arg-Nal-Gly]

cyclo[D-Tyr-His-Arg-Nal-Gly]
```

Particularly preferred oligopeptide moieties include those having a sequence selected from

```
cyclo[D-Tyr-Orn-Arg-Nal-Gly]

cyclo[D-Tyr-Orn(FB)-Arg-Nal-Gly]

cyclo[D-Tyr-(Me)D-Orn(FB)-Arg-Nal-Gly]
```

In preferred embodiments, the label is a radiolabel. The label may be covalently attached directly to the ligand, or may be attached (e.g., in the case of a metal radiolabel) by means of a complexation agent which is covalently attached to the ligand. When a spacer group is used, as described above, the complexation agent may be attached via the nucleophilic group at the distal end of the spacer. Other intermediate groups to facilitate indirect attachment between the ligand and the label would be apparent to the person of ordinary skill in the art.

The cyclic pentapeptide cyclo(D-Tyr-Arg-Arg-Nal-Gly) (also known as CPCR4 or FC131) binds to CXCR4 with high affinity. It is also relatively easy to radiolabel, e.g. by using iodine radionuclides attached to the tyrosine residue. In preliminary animal studies, radiolabeled CPCR4 showed around 10 times increased accumulation in CXCR4+ tumors compared to control tumors. The pharmacokinetic and other properties of CPCR4 may be altered by modification of the amino acid residues. In particular, N-methylation of an Arg residue, the substitution of $Arg^1$ for another cationic amino acid (e.g. ornithine), the insertion of Ala between Nal and Gly and the N-methylation of Tyr in the resulting hexapeptides all lead to modified CXCR4 antagonists maintaining useful affinity for the receptor.

Preferably, the compound does not include an antibody or fragment thereof as part of its structure.

In certain compounds of the invention, the radiolabel may be selected from $^{18}F$, $^{123}I$, $^{124}I$ and $^{125}I$. $^{123}I$ is particularly useful when the compound is to be used for in vivo single photon emission computed tomography (SPECT) studies. $^{125}I$ may be preferred for in vitro or ex vivo uses of the compound. $^{18}F$ and $^{124}I$ are particularly useful for in vivo studies using positron emission tomography (PET) imaging.

When the compound of the invention contains one or more Dap(FB), Dap(FP), Dab(FB), Dab(FP), FB or FP groups, the fluorine substituent may be $^{18}F$. This presents a convenient means for radiolabelling such compounds. In preferred compounds of this type, the $^{18}F$ is present on an FB or FP substituent at $N^\delta$ of Orn or D-Orn.

Alternatively, the radiolabel may be selected from $^{211}At$, $^{225}Ac$, $^{211}Bi$ and $^{212}Bi$. These radionuclides are all relatively low-range α-emitters which allow the compounds of the invention to be used for targeted radiotherapy. The low-range emission provides a safer radiotherapeutic approach for metastases. For radiotherapy of primary tumors using compounds of the present invention, it may be preferred to use a radionuclide with longer-range emission and hence, in this case, the radiolabel may be selected from beta-emitters with low and higher range, e.g. $^{177}Lu$ or $^{90}Y$, $^{188}Re$ and $^{131}I$, respectively.

In general, useful diagnostic isotopes (for PET and SPECT-based detection and imaging) for use in accordance with the present invention include: $^{18}F$, $^{47}Sc$, $^{51}Cr$, $^{52}Fe$, $^{52m}Mn$, $^{56}Ni$, $^{57}Ni$, $^{62}Cu$, $^{64}Cu$, $^{67}Ga$, $^{68}Ga$, $^{72}As$, $^{75}Br$, $^{76}Br$, $^{77}Br$, $^{82}Br$, $^{89}Zr$, $^{94m}Tc$, $^{97}Ru$, $^{99m}Tc$, $^{111}In$, $^{123}I$, $^{124}I$, $^{131}I$, $^{191}Pt$, $^{197}Hg$, $^{201}Tl$, $^{203}Pb$, $^{110m}In$, $^{120}I$.

In general, useful therapeutic isotopes for use in accordance with the present invention include: $^{32}P$, $^{67}Cu$, $^{77}As$, $^{90}Y$, $^{99}Mo$, $^{103}Ru$, $^{105}Rh$, $^{109}Pd$, $^{111}Ag$, $^{114m}In$, $^{117m}Sn$, $^{121}Sn$, $^{127}Te$, $^{131}I$, $^{140}La$, $^{140}Nd$, $^{142}Pr$, $^{143}Pr$, $^{149}Tb$, $^{149}Pm$, $^{151}Pm$, $^{153}Sm$, $^{159}Gd$, $^{161}Tb$, $^{166}Ho$, $^{166}Dy$, $^{169}Er$, $^{169}Yb$, $^{172}Tm$, $^{175}Yb$, $^{177}Lu$, $^{186}Re$, $^{188}Re$, $^{198}Au$, $^{199}Au$, $^{211}At$, $^{211}Bi$, $^{212}Bi$, $^{213}Bi$, $^{225}Ac$.

In certain compounds of the invention, the radiolabel is bound to the ligand by means of a complex between an organic complexation agent and a radionuclide, the complex being bound to the ligand in such a way as not to destroy its binding properties at the CXCR4 receptor. In such embodiments, the complexation agent is preferably covalently bound to the ligand, whilst the radiolabel may be covalently or non-covalently bound to the complexation agent.

The use of complexation agents broadens the range of radionuclides which may be bound to the compounds of the invention. Preferred complexation agents include DOTA (1,4,7,10-tetraazacyclododecane-N,N',N'',N'''-tetraacetic acid) and derivatives thereof, TETA (1,4,8,11-tetraazacyclotetradecane-1,4,8,11-tetraacetic acid), DTPA (diethylene triamine pentaacetic acid) and HYNIC (hydrazinonicotinamide). The complexation agents may be bound to appropriate side chains of the amino acids of the cyclic oligopeptides of the invention, or to linker groups bound to appropriate side chains of the amino acids of the cyclic oligopeptides of the invention, i.e. so as to minimise disruption of the CXCR4-binding properties of the compound. Alternatively, intervening spacer groups can be employed, as described above.

It is also possible to modify the compounds of the invention by the addition of one or more hydrophilic moieties (e.g. carbohydrates or polyethylene glycol chains). Such modifications can be used to improve the pharmacokinetics of the compounds in vivo. For example, a carbohydrate-modified peptide-based compound of the invention is expected to exhibit reduced hepatic uptake and thus, compared with a lipophilic peptide, should show somewhat delayed blood clearance and predominantly renal excretion following administration. This leads to the generation of an image which is obtainable soon after administration and which is expected to be higher in contrast between CXCR4 positive and CXCR4 negative tissues.

In accordance with a second aspect of the present invention, there is provided a compound, or a pharmaceutically acceptable salt or ester thereof, comprising a cytotoxic moiety and a ligand for the chemokine receptor CXCR4, the ligand having a binding affinity for the CXCR4 receptor, measured as IC50 in the presence of $^{125}$I-CPCR4, of 250 nM or lower, wherein the ligand comprises a cyclic oligopeptide moiety having the motif B-Arg or B-(Me)Arg within the cyclic moiety, and wherein B is a basic amino acid, a derivative thereof, or phenylalanine, provided that the motif is B-Arg when B is a $N^\alpha$-methyl derivative of a basic amino acid.

The optional and preferred features of the compounds of the first aspect of the invention are also to be understood to be preferred, as appropriate, in compounds of this second aspect. In particular, the cytotoxic moiety may be bound directly to the ligand or may be attached via a spacer group. Compounds of this aspect of the invention may be used for the targeted chemotherapy of tumours having metastatic potential, and their associated metastases, as a result of the relatively high expression of CXCR4 by such tissues. Preferred cytotoxic moieties may be selected from any of those cytotoxic compounds generally used for chemotherapy of the tumour concerned.

In accordance with a third aspect of the invention, there is provided a compound, or a pharmaceutically acceptable salt or ester thereof, comprising a ligand for the chemokine receptor CXCR4, the ligand having a binding affinity for the CXCR4 receptor, measured as IC50 in the presence of $^{125}$I-CPCR4, of 250 nM or lower, wherein the ligand comprises a cyclic oligopeptide moiety having the motif B-Arg or B-(Me)Arg within the cyclic moiety, and wherein B is a basic amino acid, a derivative thereof, or phenylalanine, provided that the motif is B-Arg when B is a $N^\alpha$-methyl derivative of a basic amino acid, and provided that the cyclic oligopeptide moiety does not have the sequence cyclo[D-Tyr-Arg-Arg-Nal-Gly], nor the sequence cyclo[D-Tyr-Orn-Arg-Nal-Gly].

The compounds of the third aspect of the invention are useful for labeling for use in diagnostics and imaging. They may also be coupled to cytotoxic moieties for targeted chemotherapy of CXCR4-positive tumours. Furthermore, they may also be used for chemotherapy on their own since they are capable of antagonistic properties at the CXCR4 receptor. The optional and preferred features of the compounds of the first aspect of the invention are also to be understood to be preferred, as appropriate, in compounds of this third aspect.

In accordance with a fourth aspect of the invention, there is provided a compound, or a pharmaceutically acceptable salt or ester thereof, comprising a ligand for the chemokine receptor CXCR4, wherein the ligand comprises a cyclic oligopeptide moiety having the sequence:

cyclo[D-Tyr/(Me)D-Tyr-B-Arg/(Me)Arg-Z-(Ala)$_n$-X]

wherein:
B is as defined above;
Z is an amino acid containing an aromatic group in its side chain;
n is 1 or 0; and
X is selected from Gly, (Me)Gly, Ala, Dap, Dap(FP), Dab, Dab(FP), Dab(FB) and Dap(FB), the compound optionally comprising a detectable label, provided that, when the compound does not comprise a detectable label, the cyclic oligopeptide moiety does not have the sequence cyclo[D-Tyr-Arg-Arg-Nal-Gly], nor the sequence cyclo[D-Tyr-Orn-Arg-Nal-Gly].

In this fourth aspect, Z may be selected from Nal, Dap(FB), AMS (FB), and (Me)Nal. Z is preferably Nal. Preferably, n is 1 only when the preceding four amino acids in the cyclic moiety sequence are D-Tyr/(Me)D-Tyr-Arg-Arg-Nal. Preferably, Z is Me(Nal) only when B is Me(Arg). The other preferred and optional features of the first, second and third aspects of the invention are also applicable to this fourth aspect, as appropriate. In particular, When B is Orn or D-Orn, the ornithine residue may be substituted at $N^\delta$ with one or two groups which may be selected from fluorobenzoyl (FB), fluoropropionyl (FP), acetyl (Ac), palmitoyl (Palm; e.g. so as to form the peptide cyclo[D-Tyr-Orn(Palm)-Arg-Nal-Gly]), amido (Am) (i.e. so as to form a urea-type moiety), methyl (Me), 1-naphthylmethyl (N1), 2-naphthylmethyl (N2), benzyl (Bz) and acyl spacer moieties. Preferably, the acyl spacer moiety is an acyl group containing a chain of 1-16 carbons, more preferably 1-14 carbons, optionally interrupted by heteroatoms, and preferably having a nucleophilic functional group at its end distal to the ornithine $N^\delta$. The nucleophilic functional group may be, for example, an amino or hydroxyl group. This group enables further moieties to be added to the end of the spacer, the purpose of the spacer being to minimise the effects of any additional groups on the CXCR4 binding capability of the cyclic oligopeptide. The acyl spacer moiety may be selected from aminohexanoyl (Ahx), triethyleneglycolamino acyl (TGAS, i.e. —COCH$_2$(OCH$_2$CH$_2$)$_2$NH$_2$), (Ahx)$_2$, (Ahx)$_3$, (TGAS)$_2$ and (TGAS)$_3$. When multimers of these spacers are present, the repeating units are joined together by amide bonds. Currently preferred spacer groups are Ahx, TGAS, (Ahx)$_3$, (TGAS)$_2$ and (TGAS)$_3$. The substituents described for ornithine, including the acyl spacer moieties, may also be employed when B is Lys, Dap or Dab. In such cases, the spacer moiety preferably has a nucleophilic functional group at its end distal to its point of attachment to the oligopeptide (i.e., the $N^\epsilon$ when B is Lys).

In accordance with a fifth aspect of the invention, there is provided a pharmaceutical composition comprising a compound of the invention as described in the first, second, third or fourth aspects above, together with one or more pharmaceutically acceptable excipients. Preferably, the composition is suitable for injection.

Pharmaceutical compositions of this invention comprise any of the compounds of the present invention, or pharmaceutically acceptable salts or esters thereof, with any pharmaceutically acceptable carrier, adjuvant or vehicle. Pharmaceutically acceptable carriers, adjuvants and vehicles that may be used in the pharmaceutical compositions of this invention, depending on the intended formulation and route of administration, include, but are not limited to, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, rectally, nasally, buccally, vaginally or via an implanted reservoir. As mentioned above, parenteral administration is preferred. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques. For most applications, intravenous or intralesional (e.g. intratumoral) injection is envisaged.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol solution, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions.

These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

In a further aspect, the present invention provides a method of synthesis of a compound according to the first aspect of the invention as described above, the method comprising treating the ligand with a source of the detectable label under conditions such that the detectable label, or a complex between an organic complexation agent and the label, becomes bound to the ligand.

In yet another aspect, the present invention provides a method of synthesis of a compound according to the second aspect as described above, the method comprising treating the ligand with a source of the cytotoxic moiety under conditions such that the cytotoxic moiety becomes bound, directly or indirectly, to the ligand.

The present invention also provides a compound according to the invention as described above, for use in therapy or diagnosis.

In a related aspect, the invention also provides the use of a compound according to the invention as described above in the preparation of a medicament for the treatment of a neoplastic condition.

By targeting appropriate radionuclides or cytotoxic components to CXCR4 receptor-bearing tissues, it should be possible to provide a relatively selective chemotherapy of neoplasias having metastatic potential. Any metastases or circulating tumor cells resulting from such tumors should also be targeted by the targeted radionuclide or cytotoxic component.

In a further aspect, the present invention provides the use of a compound as described above in relation to the first aspect of the invention in the preparation of a medicament for the diagnostic imaging of a neoplastic condition. In preferred embodiments of this aspect of the invention, the neoplasia has, or is suspected of having, metastatic potential. In certain embodiments, the neoplastic condition may be breast or prostate cancer.

As mentioned above, the compounds of the first aspect of the invention provide a highly useful tool for the selective detection and imaging of cells bearing CXCR4 receptors and hence having metastatic potential. The compounds may be administered by routine methods (e.g. i.v. injection) and images of the patient may be taken after a short time, by which stage any tissues having a relatively high expression of CXCR4 will show a relative concentration of the detectable compound of the invention.

In a related aspect, the invention also provides a method of imaging neoplastic tissue, the method comprising the administration, to a subject having (or suspected of having) a neoplasia, of a compound according to the first aspect of invention, and the detection of the compound following distribution thereof in vivo.

The said method of imaging preferably includes the further step, following the detection step, of generating an image of the detected distributed compound. The detection step may in particular be performed using PET or single photon emission computed tomography (SPECT) when the label is a radionuclide. When magnetic or paramagnetic labels are employed, magnetic resonance imaging is preferred.

In accordance with yet another aspect, the present invention provides a method of determining the metastatic potential of cells of a neoplasia, the method comprising exposing the cells to a compound according to the first aspect of the present invention, or a composition as described above, so as to allow the compound to bind to CXCR4 receptors on the surface of the cells, removing unbound compound from the vicinity of the cells, and determining the presence and/or amount of compound bound to the cells.

The said method of determining the metastatic potential of cells may be carried out in vivo or in vitro (i.e. using a sample of cells or tissue removed from a patient).

When the method of determining the metastatic potential of cells is carried out using a compound according to the first aspect of the invention, the imaging, or the determination of the presence and/or amount of bound compound, may in particular be performed using PET or single photon emission computed tomography (SPECT) when the label is a radionuclide. When magnetic or paramagnetic labels are employed, magnetic resonance imaging is preferred.

Other detectable labels for use in the compounds of the present invention include fluorescent components (e.g. green fluorescent protein (GFP), rhodamine).

The invention additionally provides, in yet another aspect, a method of treatment of a neoplastic condition in a subject, the neoplasia having, or being suspected of having, metastatic potential, the method comprising the administration to the subject of a compound according to the invention, or a composition as described above. In certain embodiments, the neoplastic condition may be breast or prostate cancer.

The invention will now be described in more detail by way of example only and with reference to the appended drawings.

EXAMPLE 1

Figure 1:
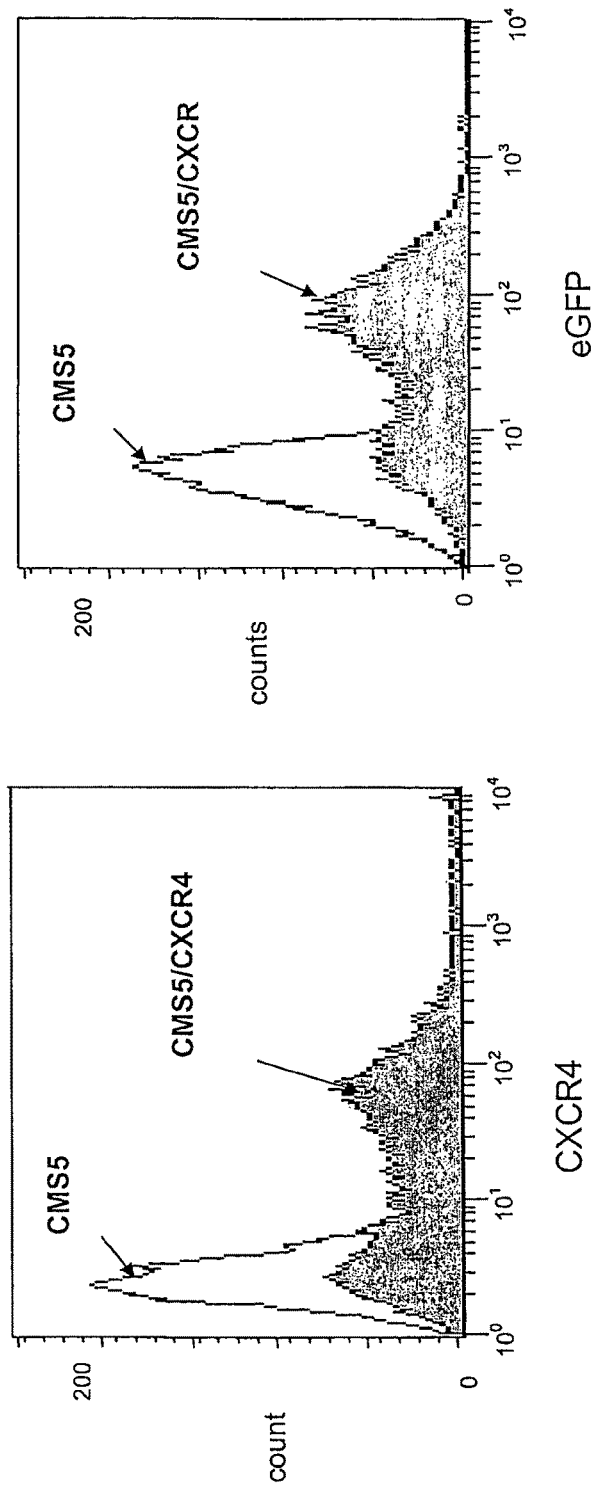
FIG. 1 shows the fluorescence-activated cell sorting (FACS) results from transfection of cells in vitro with a vector coding for CXCR4 and a GFP reporter.

Radiolabeled CPCR4 SPECT/PET Imaging 1.1 Summary 1.1.1 Materials and Methods

A method for early assessment of the metastatic potential of tumors would be a valuable tool for therapy prediction and control. Recently a key role in metastasis was attributed to the chemokine receptor CXCR4. In a variety of tumors such as breast and prostate cancer, CXCR4 has been found to play a dominating role during tumor cell homing and was shown to be expressed, both in primaries and metastases. The aim of this study was to develop a novel radiolabeled probe for the in vivo imaging of CXCR4 expression on tumors and metastases by SPECT and PET imaging.

CPCR4, a cyclic peptide (cyclo(D-Tyr-Arg-Arg-Nal-Gly), was radiolabeled and evaluated in binding assays on CXCR4-expressing Jurkat cells. The tumorigenic fibrosarcoma cell line CMS5 was retrovirally transduced for stable CXCR4/GFP expression and characterized in fluorescence-activated cell sorting (FACS) and radioligand binding assays. Biodistribution studies and SPECT/PET imaging were carried out in CMS5/CXCR4$^+$ mice. Tumors were further analyzed by autoradiography, IHC and GFP fluorescence.

1.1.2 Results and Conclusions

Radiolabeled CPCR4 binds with high affinity ($K_D$: 0.4±0.1 nM) and specificity (>90%) in an antagonistic manner to endogenously CXCR4-expressing Jurkat cells and to transduced CXCR4/GFP-expressing CMS5 cells. CMS5/CXCR4$^+$-fibrosarcomas were found to be a reliable CXCR4 tumor model in mice, as confirmed by autoradiography, immunohistochemistry (IHC) and GFP fluorescence. Biodistribution studies of i.v. injected radiolabeled CPCR4 showed 1 h post-injection 5.5±1.5% ID/g (injected dose/g) in the CMS5/CXCR4$^+$ tumor and 0.6±0.2% ID/g in the CMS5/CXCR4$^-$ control. Besides a rapid blood clearance and a low background accumulation (<1.0% ID/g) a higher tracer uptake was found in the liver 19.5±2.8% ID/g, intestine 17.2±2.9% ID/g and kidneys 12.2±2.3% ID/g. Using CPCR4-SPECT and animal PET imaging of mice, a clear delineation of CXCR4$^+$ tumors was possible, whereas no activity accumulation was visible for CXCR4$^-$ controls in the same animals.

In this study we succeeded in the development of the first radiolabeled probe for in vivo targeting of the CXCR4 chemokine receptor. The tracer binds with high affinity and specificity in an antagonistic manner to its binding site and allowed a clear delineation of CXCR4$^+$ tumors in vivo. We hypothesize that this new class of tracers will be very promising probes for the investigation of the metastatic potential of tumors and early imaging and radionuclide therapy of metastatic processes.

1.2 Detailed Description of Example 1

1.2.1 Materials and Methods 1.2.1.1 Peptide Synthesis and Radiolabeling

Peptides were synthesized by using standard solid-phase peptide synthesis protocols according to the Fmoc strategy. The Fmoc amino acids Fmoc-Arg(Pbf), Fmoc-D-Tyr(tBu) and Fmoc-Gly were purchased from Novabiochem (Bad Soden, Germany), Fmoc-2-naphthylalanine was obtained from Bachem (Bubendorf, Switzerland). Peptide synthesis was performed manually on a TCP (trityl chloride polystyrene) resin. O-(1H-benzotriazol-1-yl)-N,N,N',N'-tetramethyluronium tetrafluoroborate (TBTU) and diphenyl phosphoryl azide (DPPA) were purchased from Alexis and Aldrich (Steinheim, Germany), respectively. IodoGen (1,3,4,6-tetrachloro-3R,6R-diphenylglycoluril) was obtained from Pierce (Rockford, Ill., USA), sodium iodide-125 was purchased from Hartmann-Analytic GmbH (Braunschweig, Germany) and sodium iodide-123 was obtained from Amersham Health (Eindhoven, The Netherlands). Sodium iodide-124 was kindly provided by Prof. W. Brandau (Essen, Germany). All other reagents were purchased from Merck (Darmstadt, Germany) or Sigma-Aldrich (Taufkirchen, Germany). Unless specified otherwise, solvents were used without further purification.

The synthesis of the cyclic pentapeptide CPCR4 and derivatives thereof was performed as described recently with small modifications. [1, 2] In brief, after attachment of Fmoc-Gly-OH to the TCP-resin the remaining amino acids were coupled after activation with TBTU and subsequent deprotection of the Fmoc group by using 20% piperidine in DMF, respectively. After peptide chain assembly, the resin-bound peptides were treated with of a mixture of acetic acid, 2,2,2-trifluoroethanol and dichloromethane (2:2:6) for 2 h at room temperature. Afterwards the resin was filtered and washed twice with the cleavage mixture. The combined filtrates were evaporated in the presence of petrol ether in vacuum.

For cyclization the side chain protected peptides were dissolved in DMF at a concentration of 2.5 mM. At −40° C., 5 equiv. $NaHCO_3$ and 3 equiv. DPPA were added and the solution was stirred overnight with warming to room temperature. After filtration of the solid $NaHCO_3$, DMF was evaporated in vacuum. The residue was triturated with water, filtered and washed with water and diethyl ether. The frilly protected cyclized peptides were treated with of a solution of 95% TFA and 5% water for 2 hours at room temperature. The deprotected peptide was precipitated from ice cold diethyl ether and centrifuged at 5° C. For the synthesis of the non-radioactive iodinated reference peptide the amino acid building block Fmoc-D-3-iodo-Tyr-OH was synthesized as described previously. [2] For the incorporation of this amino acid and subsequent peptide cyclization, PyBOP (Benzotriazol-1-yl-oxytripyrrolidinophosphonium hexafluorophosphate)/collidine activation was used. Afterwards the crude cyclic peptides were lyophilized and purified by preparative RP-HPLC. Finally, the peptides were characterized by analytical HPLC and HPLC-ESI/MS on a LCQ LC-MS system from Finnigan (Bremen, Germany) using the Hewlett-Packard series 1100 HPLC system.

Additional details of the peptide syntheses are as follows:
Materials and Methods
General All commercially available chemical reagents were used without further purification. Technical solvents were distilled before use.

Trityl resins were purchased from PepChem and amino acid derivatives from Iris Biotech GmbH, NovaBiochem, Merck, Bachem, Neosystem, Aldrich, while all other chemicals were bought from Aldrich, Fluka or Merck if not stated otherwise.

NMP (N-methylpyrrolidone) was obtained from BASF and used without further distillation. Dry solvents were purchased from Aldrich, Fluka or Merck. Dry dichloromethane was distilled from calcium hydride under argon and kept over a 4 Å molecular sieve. Water for RP-HPLC was filtered through a 0.22 μm filter (Millipore, Millipak40).

RP-HPLC analyses were performed using an Omnicrom YMC column (4.6 mm×250 mm, 5 μm $C_{18}$, 1 mL/min). The eluent was a linear gradient from water (0.1% TFA) to acetonitrile (0.1% TFA) over 30 minutes (10% to 100%, 10% to 60%, and 20% to 50%) and detection at 220 nm and 254 nm. The retention time ($R_t$) of the analytical RP-HPLC is given in minutes with the gradient in percentage of acetonitrile. Semi-preparative RP-HPLC was done on a Beckman System Gold equipped with high pressure module 125, UV-detector 166, and using an Omnicrom ODS-A C18 (120 Å, 5 μm, 250 mm×20 mm) column in combination with the same solvents as stated above.

NMR spectra were recorded on a Bruker Avance 250 or Bruker DMX 500 at 298K. The chemical shifts are reported in ppm on the δ scale relative to the solvent signal used. $^{13}$C-NMR-spectra were recorded using $^1$H-broad band decoupling. Pulse programs were taken from the Bruker library or developed by the inventors. Samples were prepared in tubes with a diameter of 5 mm using 0.5 ml of deuterated solvent. The resulting spectra were processed on a PC workstation using Bruker TOPSPIN 1.3 software.

ESI mass spectra were recorded on a Finnigan LCQ in combination with an Agilent/HP 1100 RP-HPLC system using an Omicrom YMC ODS-A C18 column (120 Å, 3 μm, 125 mm×2 mm) with a flow rate of 0.2 mL/min. The eluent was a linear gradient (10% to 100% acetonitrile) from water to acetonitrile with 0.1% formic acid over 20 min with detection at 220 nm.

Loading of TCP-Resin (General Procedure)

Peptide synthesis was carried out using TCP-resin (1 mmol/g) following standard Fmoc-strategy [13]. Fmoc-Xaa-OH (1.2 eq.) were attached to the TCP resin with DIEA (diisopropylethylamine) (2.5 eq.) in anhydrous DCM (2 mL) at room temperature for 1 h. The remaining trityl chloride groups were capped by addition of a solution of MeOH, DIEA (5:1; v:v) for 15 min. The resin was filtered and washed thoroughly with DCM (5×) and MeOH (3×). The loading capacity was determined by weight after drying the resin under vacuum and ranged from 0.4-0.9 mmol/g.

Fmoc Deprotection (General Procedure)

The resin-bound Fmoc peptide was treated with 20% piperidine in NMP (v/v) for 10 minutes and a second time for 5 minutes. The resin was washed with NMP (5×).

TBTU/HOBt Coupling (General Procedure)

A solution of Fmoc-Xaa-OH (2 eq.), TBTU (2 eq.), HOBt (hydroxybenzotriazole) (2 eq.), DIEA (5.2 eq.) in NMP was added to the resin-bound free amine peptide and shaken for 60 min at room temperature and washed with NMP (5×).

o-Nitrobenzenesulfonyl (o-Ns) Protection

N-alkylation was carried out using an optimized protocol [14]. A solution of o-Nitrobenzenelsulfonyl chloride (o-Ns-Cl) (5 eq.) and collidine (10 eq.) in NMP was added to the resin-bound free amine peptide and shaken for 15 min at room temperature. The resin was washed with NMP (3×) and dry THF (3×).

N-Alkylation under Mitsunobu Conditions

A solution of triphenylphosphine (5 eq.), DIAD (diisopropyl azodicarboxylate) (5 eq.) and alcohol (10 eq.) in dry THF was added to the resin-bound o-Ns-protected peptides and shaken for 10 min at room temperature. The resin was filtered off, and washed with dry THF (3×) and NMP (3×).

o-Ns Deprotection

For o-Ns deprotection, the resin-bound N-alkyl-N-o-Ns-peptides were treated with a solution of mercaptoethanol (10 eq.) and DBU (5 eq.) in NMP for 5 minutes. The deprotection procedure was repeated one more time and the resin was washed with NMP (5×).

HATU/HOAt Coupling (General Procedure)

A solution of Fmoc-Xaa-OH (2 eq.), HATU (2 eq.), HOAt (hydroxyazobenzotriazole) (2 eq.), DIEA (4 eq.) in NMP was added to the resin-bound $N^\alpha$-methylamine free peptides and shaken for 3 hours at room temperature and washed with NMP (5×).

Alloc Deprotection $Pd(PPh_3)_4$ (0.125 eq.) in dry DCM (0.5 ml/g resin) was added to the resin-bound Alloc (allyloxycarbonyl) peptide followed by an addition of phenylsilan in dry DCM (0.5 ml/g resin) and shaken for 1 hour. The resin was washed 5 times with DCM.

Peptide Cleavage

For complete cleavage from the resin the peptides were treated three times with a solution of DCM and HFIP (4:1; v:v) at room temperature for half an hour and the solvent evaporated under reduced pressure.

Cyclization

To a 1 mM solution of peptide and NaHCO$_3$ (5 eq.) DPPA (diphenylphosphorylazide) (3 eq.) was added at room temperature and stirred over night or until no linear peptide could be observed by ESI-MS. The solvent was evaporated to a small volume under reduced pressure and the peptides precipitated in saturated NaCl solution and washed two times in HPLC grade water.

Removal of Acid Labile Side Chain Protecting Groups

Cyclized peptides were stirred in a solution of TFA, water and TIPS (triisopropylsilane) (95:2.5:2.5) at room temperature for one hour or until no more protected peptide could be observed by ESI-MS and precipitated in diethylether and washed two more times.

Acylation in Solution

For ornithine side chain acylation cyclized and fully deprotected peptides were stirred with TBTU (1 eq) and the corresponding acid (1 eq) in DMF for 15 minutes. The solution was directly injected into the HPLC for purification.

Amino Acid Synthesis $N^\alpha$-Alloc-$N^\epsilon$-Boc-L-ornithine $N^\epsilon$-Boc-L-ornithine (1.00 g, 4.3 mmol) was dissolved in a solution of Na$_2$CO$_3$ (1.14 g, 10.75 mmol) in water and THF (50 ml, 1:1, v/v). After addition of allyl chloroformate (0.46 ml, 4.3 mmol) the solution was stirred for 1.5 h. The THF was evaporated under reduced pressure and the aqueous phase washed with diethylether (1×50 mL), acidified with conc. HCl to pH 1 and the product extracted with EtOAc (3×50 mL). The combined organic layers were dried (Na$_2$SO$_4$), filtered, concentrated and dried in vacuo to give a colourless, sticky oil as sufficiently pure product (1.20 g, 90%). $^1$H NMR (250 MHz, DMSO-d$_6$): δ 12.52 (s, 1H, OH), 7.49 (d, 7.72 Hz, 1H, NH$^\alpha$), 6.78 (t, 5.05 Hz, 1H, NH$^\epsilon$), 5.91 (br m, 1H, CH$^{Alloc}$), 5.30 (dd, 17.15 Hz, 1.69 Hz, H$^{AllocTerm1}$), 5.19 (dd, 10.17 Hz, 1.68 Hz, H$^{AllocTerm2}$), 4.48 (m, 2H, CH$_2^{Alloc}$), 3.91 (br m, 1H, H$^\alpha$), 2.91 (m, 2H, H$^\beta$), 1.81-1.40 (br m, 4H, H$^\gamma$, H$^\delta$), 1.38 (s, 9H, H$^{Boc}$). $^{13}$C NMR (250 MHz, DMSO-d$_6$): 174.4, 156.5, 156.1, 134.1, 117.4, 77.9, 65.1, 60.2, 54.1, 28.8, 26.7, 14.6. RP-HPLC: 16.7 min.

$N^\alpha$-Alloc-$N^\epsilon$-Fmoc-L-ornithine $N^\alpha$-Alloc-$N^\epsilon$-Boc-L-ornithine (1.20 g, 3.87 mmol) was dissolved in DCM (10 mL) and TFA (5 mL) was added slowly. After stirring for 45 min the liquid was evaporated.

The crude product was dissolved in a solution of Na$_2$CO$_3$ (1.02 g, 9.68 mmol) in water and THF (40 ml, 1:1, v/v). After addition of Fmoc-N-Oxysuccinimid (1.31 g, 3.87 mmol) the solution was stirred for 1.5 h. The THF was evaporated under reduced pressure and the aqueous phase washed with diethylether (1×50 mL), acidified with conc. HCl to pH 1 and the product extracted with EtOAc (3×50 mL). The combined organic layers were dried (Na$_2$SO$_4$), filtered, concentrated and dried in vacuo to give a colourless solid as sufficiently pure product (1.65 g, 97%). $^1$H NMR (250 MHz, DMSO-d$_6$): δ 12.52 (s, 1H, OH), 7.49 (d, 7.72 Hz, 1H, NH$^\alpha$), 6.78 (t, 5.05 Hz, 1H, NH$^\epsilon$), 5.91 (br m, 1H, CH$^{Alloc}$), 5.30 (dd, 17.15 Hz, 1.69 Hz, H$^{AllocTerm1}$), 5.19 (dd, 10.17 Hz, 1.68 Hz, H$^{AllocTerm2}$), 4.48 (m, 2H, CH$_2^{Alloc}$), 3.91 (br m, 1H, H$^\alpha$), 2.91 (m, 2H, H$^\beta$), 1.81-1.40 (br m, 4H, H$^\gamma$, H$^\delta$), 1.38 (s, 9H, H$^{Boc}$). $^{13}$C NMR (250 MHz, DMSO-d$_6$): 174.4, 156.5, 156.1, 134.1, 117.4, 77.9, 65.1, 60.2, 54.1, 28.8, 26.7, 14.6. RP-HPLC: 21.9 min.

The reaction scheme is shown below:

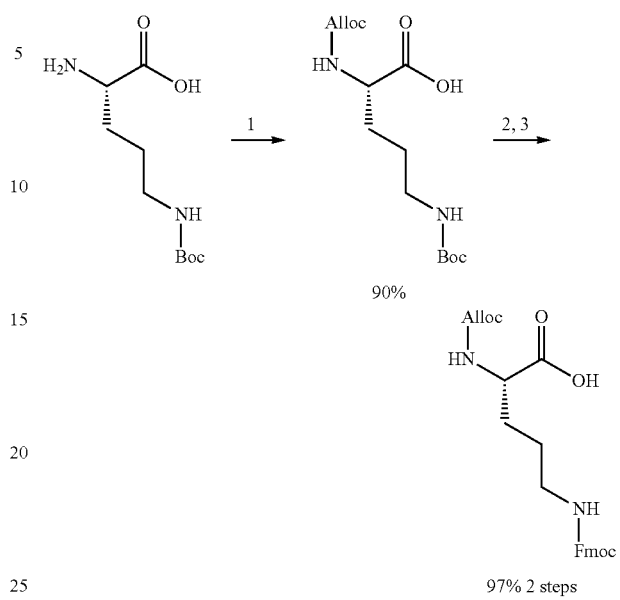

1.2.1.2 Peptide Radioiodination

CPCR4 was labeled with $^{123}$I, $^{124}$I- or $^{125}$I-iodide using the Iodogen method. [2] 0.2 mg of the peptide were dissolved in 250 µl phosphate buffered saline (PBS, pH 7.4). This solution was added to Eppendorf cups coated with 150 µg Iodogen and was combined with the radioiodide solution. After 15 min at room temperature, the solution was removed from the solid oxidizing reagent. Purification was performed using gradient RP-HPLC. Radiochemical purity was generally >95%. For animal experiments the fraction containing the radiolabeled peptide was diluted with water and bound to a Sep-Pak C18 column. Afterwards the column was washed with water and the radiolabeled peptide was eluted with methanol. After removal of the methanol in vacuum the residue was dissolved and diluted in PBS (pH 7.4). For storage at 4° C. the solution was acidified with 0.1% trifluoroacetic acid in H$_2$O containing 20% ethanol.

1.2.1.3 Lipophilicity

For the determination of the lipophilicity 0.4-2.7 µCi of $^{125}$I-CPCR4 in 500 µl PBS (pH 7.4) was mixed with 500 µl octanol and was vigorously vortexed. After centrifugation for quantitative phase separation, 100 µl from each phase were withdrawn and radioactivity was determined in a gamma counter. The experiment was performed in triplicates and repeated two times independently.

1.2.1.4 Cell Lines and Tissue Culture

The murine fibrosarcoma cell line CMS5[3] and the human 293T cell line[4] (kindly provided by R. Willemsen, Department of Clinical and Tumour Immunology, Daniel den Hoed Cancer Center, Rotterdam, The Netherlands) were both cultured in Dulbeccos's modified Eagle's medium, supplemented with 10% (v/v) fetal calf serum (PAA, Linz, Austria) and 1% (v/v) L-glutamine. The T-lymphocyte Jurkat cell line (ATCC) was maintained in RPMI 1640 medium supplemented with 10% (v/v) fetal calf serum (FCS) and 1% (v/v) L-glutamine. Media and supplements were obtained from Biochrom (Berlin, Germany), unless otherwise mentioned.

1.2.1.5 Construction of the Retroviral Vector and Target Cell Transduction

The cDNA coding for enhanced fluorescence protein was excised from pEGFP (BD Biosciences Clontech, Germany) by NcoI StuI digest, blunt ended using Klenow enzyme and inserted into the unique SmaI site of pIRESneo3 (BD Biosciences Clontech, Germany) to obtain pIRESeGFPneo3. In the next step the NotI fragment carrying IRES-eGFP was cloned into the NotI site of pBullet (Schaft et al. 2003) to obtain pBulletIRESeGFP. The 1292 by HindIII XbaI fragment of pcDNA3CXCR4[5] carrying the human chemokine receptor type 4 (CXCR4) cDNA (kindly provided by B. Moser, Bern) was isolated and cloned into the BamHI site of the retroviral vector pBulletIRESeGFP after blunt ending all sites with Klenow enzyme. The resulting vector was designated pBulletCXCR4-IRES-eGFP. Retrovirus production by transient transfection of 293T cells and transduction of CMS5 cells have been described elsewhere. [6]

1.2.1.6 FACS Sorting and Analyses

EGFP and CXCR4 expression of trypsinized cells was analyzed with a fluorescence activated cell sorter (Becton Dickinson FACS Vantage, Heidelberg, Germany) using Argon Laser beam (Spectra-Physics) of excitation energy 40 mW at 488 nm and the CellQuest Software. EGFP expression was measured directly, using FL1 (530/30 nm) filter. Dead cells were determined by addition of propidium iodide to the cells and fluorescence was determined using a FL2 585/42 nm filter. The percentage of dead cells was always ≤0.2%. The population of CXCR4 expressing CMS5 cells was enriched by sorting CXCR4-EGFP-co-expressing cells for FL1 with a minimum fluorescence of 20.

CXCR4 expression on the cell surface of trypsinized cells was determined using a phycoerythrine (PE)-labeled monoclonal rat antibody with specificity for human CXCR4 (1D9, BD Biosciences Pharmingen, Heidelberg, Germany). Trypsinized cells were washed with FACS buffer (PBS, 0.5% FCS) and $1\times10^6$ cells were stained with 0.5 µg antibody for 30 min. in the dark at 4° C. Cells were extensively washed with ice-cold FACS buffer and analyzed by flow cytometry. Nonspecific staining was assessed by PE-conjugated rat $IgG_{2b,\kappa}$ (BD Biosciences Pharmingen, Heidelberg, Germany). Detection of CXCR4 on the cell surface in the same samples as EGFP and was detected using a 575/26 nm filter (FL2). CXCR-4 staining was plotted against EGFP fluorescence (FL1).

Where indicated cells were resuspended in medium supplemented with 0.5% bovine serum albumin (BSA) (Sigma, Taufkirchen, Germany), incubated with recombinant human 100 nM SDF-1α (R&D Systems, Wiesbaden, Germany) for 1 hr at 37° C. (adapted from protocols published previously)[7, 8]; controls were incubated with diluent (PBS/ 0.1% BSA). Samples were immediately transferred to ice to avoid further internalization, centrifuged, washed with PBS/ 0.5% BSA and FACS staining for CXCR4 was performed as indicated above.

1.2.1.7 Receptor Binding Assays

For receptor binding assays cells were resuspended in PBS/0.2% BSA. A total of 200 µl of the suspension containing 400,000 cells (Jurkat, CMS5) or 200,000 cells (CMS5/CXCR4) were incubated with 25 µl of the tracer solution (containing 3.1 kBq, approx. 0.1 nM) and 25 µl of the diluent or the competitor at different concentrations. For determination of $IC_{50}$ values, $^{125}$I-CPCR4 was used as a tracer. SDF-1α was obtained from R&D Systems (Wiesbaden, Germany) and $^{125}$I-SDF-1α was purchased from Perkin-Elmer (Boston, Mass., USA). For saturation curves the tracer concentration was varied from 5 to 500 pM whereas nonspecific binding was determined in the presence of 1 µM cold CPCR4. After shaking for 2 h at room temperature, the incubation was terminated by centrifugation at 700×g and 4° C. for 4 min. Cell pellets were washed once with cold PBS followed by a second centrifugation step or for internalization studies, two times with an acidic wash buffer (20 mM NaOAc, pH5.0). Cell bound radioactivity was determined by using a gamma counter. Experiments were repeated 2-3 times in duplicates or triplicates. $IC_{50}$ values of the binding curves were calculated by nonlinear regression on a one-site or two-site competition based model using Prism 3.0 (Graph Pad Software, Inc, San Diego). $K_D$ and Bmax values were determined by nonlinear regression with the Prism 3.0 according to the manufacturer's protocol.

1.2.1.8 In Vivo Studies

For animal experiments parental CMS5 cells and transduced CMS5/CXCR4 cells were injected subcutaneously in female Swiss nu/nu mice (Charles River, France). Therefore for each mouse $1.5\times10^6$ CMS5 cells and $2\times10^6$ CMS5/CXCR4 cells were resuspended in 75 µl PBS, respectively and mixed with the same volume Matrigel-Matrix HC (BD Biosciences, Heidelberg, Germany) according to the manufacturer's protocol. Subsequently cell suspension was inoculated at each shoulder, respectively. After 14-16 days of tumour growth mice were used for imaging and biodistribution purposes. All animal experiments were approved by the local authorities and are in compliance with the institutions guidelines.

1.2.1.9 Biodistribution Studies 370 kBq (10 µCi) of $^{125}$I-labeled CPCR4 were injected intravenously into the tail vain of tumour bearing mice. The animals were sacrificed and dissected 30, 60 and 120 min after tracer injection. Organs of interest were removed and the radioactivity was measured in weighted tissue samples using the 1480 Wizard3 gamma counter from Wallac (Turku, Finland). Results are expressed as percent injected dose per gram tissue weight (% ID/g). Each value represents the mean of four to six animals.

1.2.2 Results 1.2.2.1 CPCR4-Synthesis and Radiolabeling

The synthesis of CPCR4, the cyclic pentapeptide cyclo(D-Tyr-Arg-Arg-Nal-Gly) that shows high affinity and selectivity for the CXCR4 receptor, was carried out by using standard Fmoc solid phase peptide synthesis protocols on an acid labile tritylchloride resin as described previously. [1, 2] Additional modifications by N-alkylation were done using a modified protocol designed for N-methylation via a Fukuyama-Mitsunobu reaction. [14] After peptide chain assembly the side chain protected peptide was cleaved from the resin and was cyclized using the DPPA method. [2] After removal of all protecting groups the crude cyclic pentapeptide was further purified by preparative HPLC. Analytical HPLC and HPLC/ESI-MS analyses proved homogeneity and identity of the peptides.

The radiolabeling at the Tyr side chain of CPCR4 was performed either with $^{123}$I- or $^{125}$I-iodide using the Iodogen method and subsequent separation of the unlabeled precursor by HPLC. The HPLC conditions applied allowed very efficient separation of the radioiodinated peptide from the unlabeled precursor and side products thus resulting in high radiochemical purity (>99%) and specific activity. The specific activity of the labeled peptides was assumed to be that of the radioiodide used for labeling (>2000 Ci/mmol for $^{125}$I, >5000 Ci/mmol for $^{123}$I). Whereas the radioiodide incorporation was usually >95%, the overall radiochemical yield of the $^{123}$I- and $^{125}$I-labeled peptides after HPLC purification and biocompatible formulation was in the range of 50%. After biocompatible formulation in PBS the lipophilicity of $^{125}$I-CPCR4 was determined as octanol/water (PBS) partition coefficient. A log P value of −0.04 (±0.01) was obtained.

1.2.2.2 CXCR4-Vector Construction and Viral Infection

The mouse fibrosarcoma cell line CMS5 was retrovirally transduced with CXCR4-IRES-eGFP. In the cell pool 70-80% of the retrovirally CXCR4-transduced CMS5 cells were positive for eGFP-expression as determined by FACS analysis with a mean fluorescence intensity of 130. Growth curves and survival assay (XTT) demonstrated that both cell lines had similar growth kinetics in vitro (data not shown). When CMS5 cells and CMS5/CXCR4 cells were stained for human CXCR4, CMS5 showed a background staining of 2.2% whereas 61.6% of CMS5/CXCR4 cells stained positive for human CXCR4, exhibiting a mean fluorescence intensity of 66 and 57.9% of the cells were positive for both CXCR4 and eGFP. (FIG. 1) The cell line was stable over time as indicated by repeated FACS analyses (data not shown).

1.2.2.3 Receptor Binding Studies

The suitability of $^{125}$I-CPCR4 as a novel CXCR4-radioligand was tested first at Jurkat cells that endogenously express the CXCR4 receptor [9, 10] and subsequently at CMS5/CXCR4 cells that were retrovirally transduced for CXCR4 expression. For both cell lines reproducible high specific binding was found by using $^{125}$I-SDF-1α (50-70%) and $^{125}$I-CPCR4 (>90%). At parental CMS5 cells both tracers showed negligible binding in the range of the non-specific binding of Jurkat and transduced CMS5/CXCR4 cells. From saturation binding curves nearly identical $K_D$ values in the sub-nanomolar range (0.3 to 0.4 nM) were obtained for both cell lines indicating high affinity of $^{125}$I-CPCR4 for the CXCR4 receptor. (FIG. 2 and associated Table A) Furthermore a high number of $^{125}$I-CPCR4 binding sites (Bmax) was determined. Whereas for Jurkat cells the Bmax value was more dependent on origin and varies stronger with culture conditions, the number of binding sites (Bmax) on CMS5/CXCR4 cells was constant and better reproducible (23±6 fmol receptor protein).

Figure 2A:
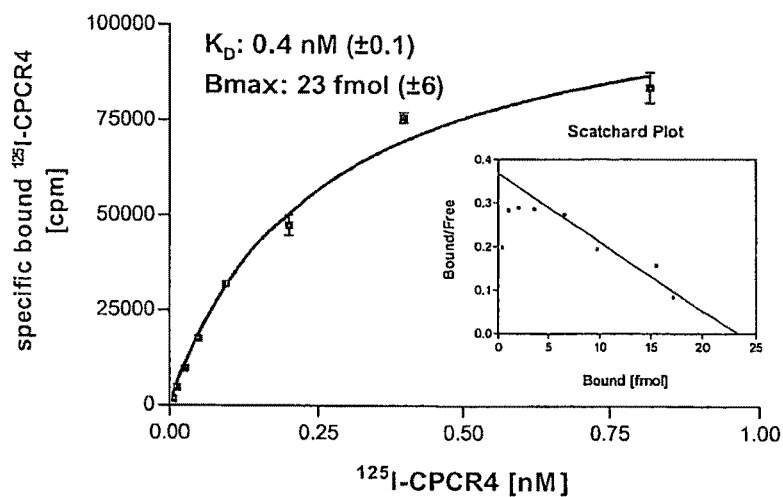
FIGS. 2a and 2b (and tables) illustrate the determination of $^{125}$I-CPCR4 binding parameters at CXCR4 on Jurkat cells and (FIG. 2b) the comparison thereof with $^{125}$I-SDF-1α.
Figure 2B:
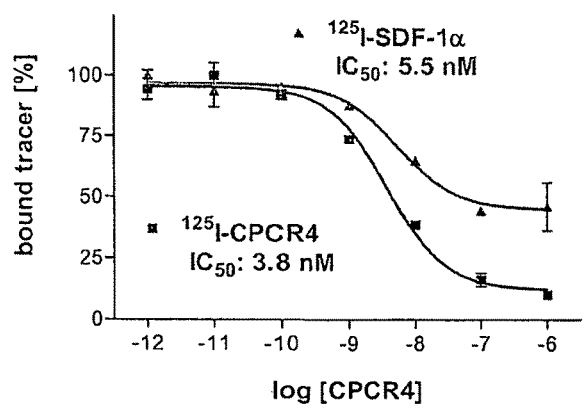

With $^{125}$I-CPCR4 as novel radioligand the affinity profile of distinct CXCR4 selective ligands was ascertained in competitive radioligand binding assays. (FIG. 2, Table B) For SDF-1α, CPCR4 and its non-radioactive iodinated reference compound Iodo-CPCR4 high affinities with nanomolar $IC_{50}$ values were found either with $^{125}$I-CPCR4 or $^{125}$I-SDF-1α at the CXCR4 receptor. In comparison with SDF-1α and the cyclic pentapeptides the CXCR4 selective bicyclam AMD3100 showed reduced affinity with both tracers. Depending on tracer and competitor two CXCR4 binding sites were monitored as reported previously. [9] For analysis of the binding curves one-site and two-site competition curve fits were used as required. The resulting high and low affinity binding sites were designated as (1) and (2). (FIG. 2, Table B).

The receptor internalization after binding of $^{125}$I-CPCR4 at the CXCR4 receptor was analyzed after two short washing steps with an acidic buffer (pH5.0). Thereafter the tracer was mostly releasable from the receptor (>80%). This indicates that no receptor internalization occurs as expected from a receptor antagonist (data not shown).

1.2.2.4 Receptor Functionality

To determine whether the human CXCR4 is functional in mouse cells, cells were pre-incubated with human SDF-1α, stained for surface CXCR4 and subsequently FACS analysis was performed. 54.7% of CMS5/CXCR4 cells stained positive for CXCR4 after pre-incubation with human SDF-1α as compared to 79.2% of control-treated cells, indicating functionality of the human receptor in murine CMS5 cells. The CXCR4-background staining in CMS5 cells decreased from 7.9 to 2.7% in the presence of SDF-1α. Jurkat cells served as positive control and did not exhibit a decrease in % positive cells, but a drop in mean fluorescence intensity from 385.4 to 155.4. In CMS5/CXCR4 cells the mean fluorescence intensity did drop from 209.0 of mock treated cells to 80.5 of SFD-1α treated cells. This indicates that Jurkat cells do contain more CXCR4 receptors than CMS5/CXCR4 cells.

1.2.2.5 In Vivo Studies

Figure 3:
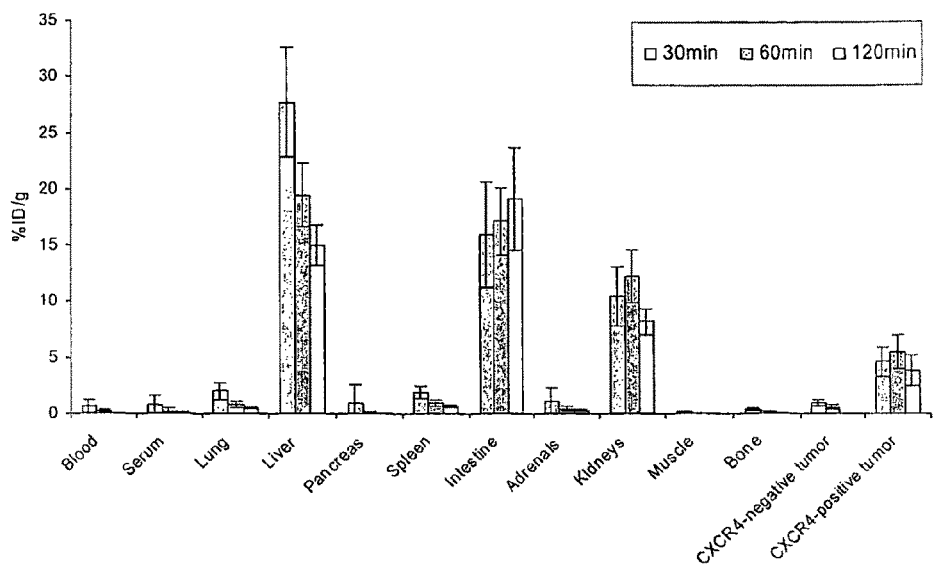
FIG. 3 (and table) illustrates the biodistribution of $^{125}$I-CPCR4 following intravenous injection thereof in nude mice.

The biodistribution and tumour accumulation of $^{125}$I-CPCR4 was determined 30, 60 and 120 min post injection in CMS5 and CMS5/CXCR4 tumour bearing nude mice. Highest tumour accumulation of $^{125}$I-CPCR4 in CMS5/CXCR4 tumours was achieved after 60 min with 5.5 (±1.5) percent of injected dose per gram (% ID/g) whereas in parental CMS5 tumours only 0.6 (±0.2) % ID/g were observed at this time. After 30 min $^{125}$I-CPCR4 shows an accumulation in CMS5/CXCR4 tumours with 4.7 (±1.3) % ID/g and after 120 min with 3.8 (±1.4) % ID/g. For all time points a higher tracer accumulation was observed only for liver, intestine and kidneys. Other organs showed only very low background accumulation. Whereas in the liver the accumulation of $^{125}$I-CPCR4 decreases with the time from 27.7 (±4.9) % ID/g after 30 min to 15.0 (±1.8) % ID/g at 120 min, the tracer accumulation in the intestine slightly increases from 16.0 (±4.7) % ID/g after 30 min to 19.2 (±4.5) % ID/g at 120 min indicative for the metabolic processes in these organs. The tracer accumulation in the kidneys shows a peak after 60 min with 12.2 (±2.3) % ID/g and decreases to 8.2 (±1.1)% ID/g after 120 min. (FIG. 3 and table)

Figure 4:
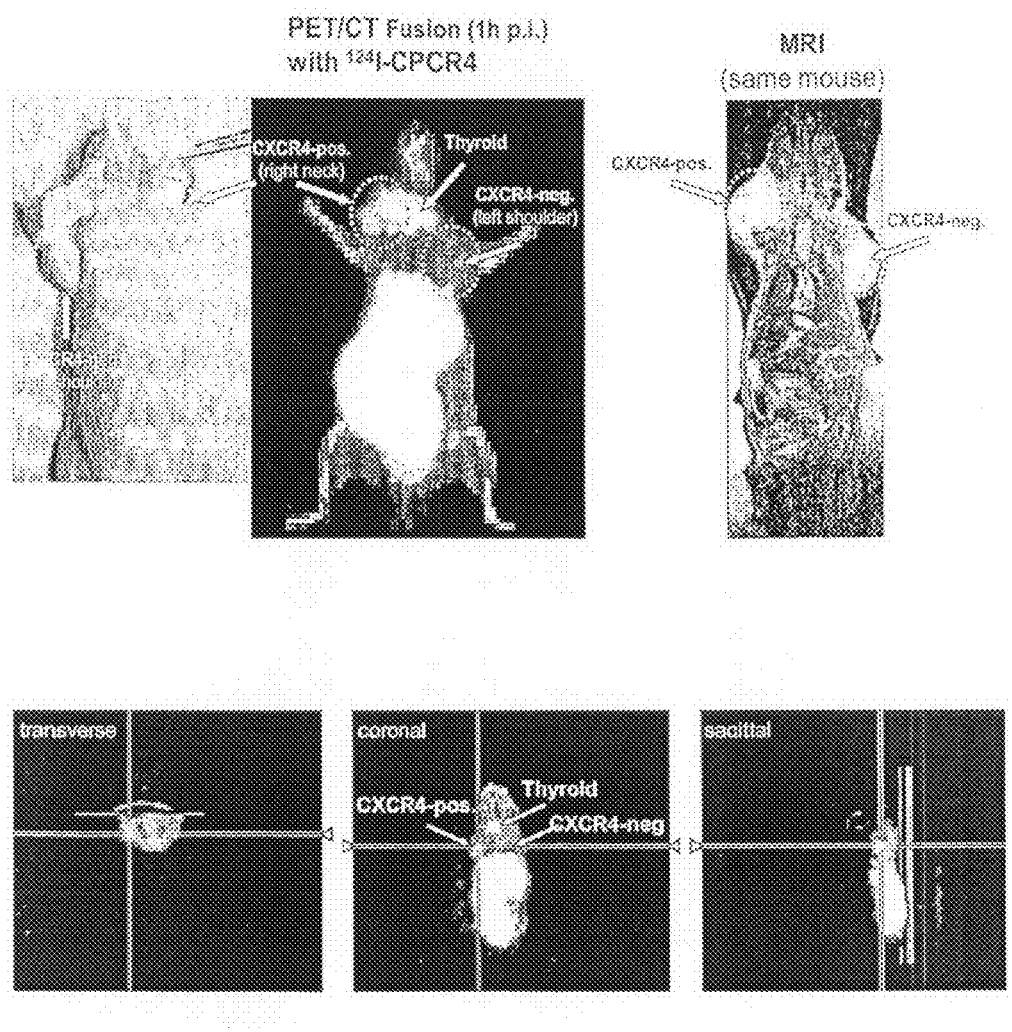
FIG. 4 shows PET/SPECT images of radiolabelled CPCR4 distribution in mice bearing CXCR4 positive and negative tumours.

FIG. 4 shows PET/SPECT results for radioiodinated-CPCR4 distribution in mice bearing both CXCR4-positive (CMS5/CXCR4) and negative (CMS5 control) tumours. A clear delineation can be observed due to the difference in CPCR4 uptake of the two types of tumour. MRI results are shown for comparison. The CXCR4 positive tumour was recognisable by PET even after 25 hr post injection. Similar results were obtained using PET with $^{18}$F-labeled radioligand, and using a gamma camera with $^{123}$I-labeling. Similarly, in ex vivo analysis of cryosections of tumours using a micro-imager, marked differences in radiation could be seen between positive and negative tumours.

EXAMPLE 2

Development of Cyclic Peptides for Targeting CXCR4 Chemokine Receptor Expression Several diseases like HIV-1 infection, cancer metastasis, rheumatoid arthritis and chronic lymphocytic B-cell leukemia are linked to the interaction of the CXCR4 chemokine receptor to its natural ligand, the 68 amino acid containing protein stromal cell-derived factor-1α (SDF-1α) [11]. One strategy for the treatment of these diseases could be to block the interaction between CXCR4 and SDF-1α with small CXCR4 antagonists. Furthermore, radiolabeling of suitable compounds with appropriate radioisotopes could provide agents for imaging of CXCR4 expression in vivo via PET.

Previous studies by Fujii et al. on CXCR4 antagonists led to the high affinity cyclic pentapeptide CPCR4, having the sequence cyclo[Gly-D-Tyr-Arg-Arg-Nal] [1]. To further improve this structure, different approaches have been chosen with respect to metabolic stability, bioavailability, conformational rigidity and chemical versatility for radiolabeling.

First, an N-methyl scan of the backbone amides was performed to influence conformational freedom and to increase metabolic stability and bioavailability. $N^α$-methylation of arginine residues yielded peptides with useful affinity ($IC_{50}$ values of 23 nM (N-Me)Arg$^3$ and 31 nM (N-Me)Arg$^4$, respectively, with Arg residues numbered according to their position in the sequence as set out in the preceding paragraph) whereas N-methylation of other amino acids noticeably decreased the affinity ($IC_{50}$>100 nM). By substitution of Arg$^3$ by ornithine, the affinity was mostly retained [12]. The delta-amino group of Orn can be alkylated or acylated via radiolabeled groups containing short lived isotopes. Moreover, the bioavailability should be improved as the high basicity of the two guanidino groups could be reduced. First ornithine-acylated derivatives showed $IC_{50}$ values between 11 and 35 nM enabling for the first time $^{18}$F-radiolabeling of small CXCR4 antagonists for PET imaging in vivo. The panel below shows the results obtained with cyclic Orn-containing pentapeptides in which the Orn is delta-N substituted with FB, FP, Ac and Am, respectively.

Affinities of Various CXCR4 Antagonists

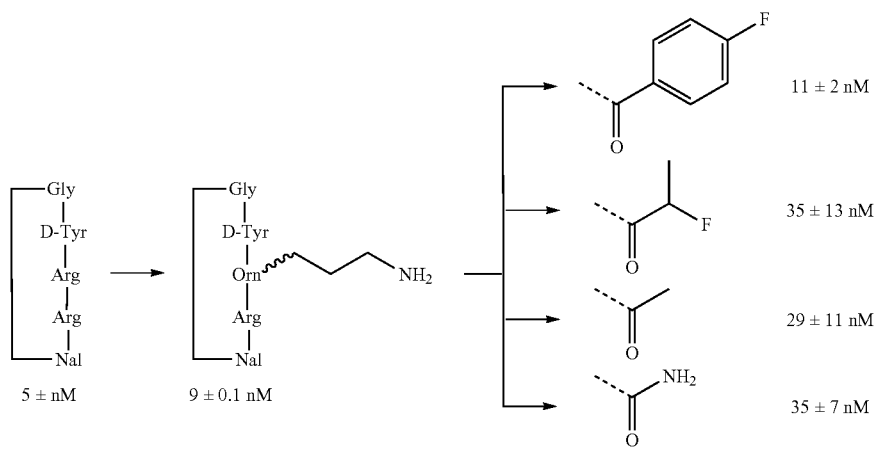

The results of binding assays with $N^\alpha$-monomethylated cyclic pentapeptides ($N^\alpha$-methyl scan) are shown in Table 1 below (note that in the following tables, peptides having $IC_{50}$ values >250 nM, and thus not falling within the first to third aspects of the present invention, are included for comparative purposes and are marked with * after the $IC_{50}$ value):

TABLE 1

| Code | Sequence | $IC_{50}$ [nM] | Calculated mass | Observed m/z (m + H) |
|---|---|---|---|---|
| CPCR4* | cyc[D-Tyr-Arg-Arg-Nal-Gly] | 4 | | |
| OD1 | cyc[D-Tyr-(Me)Arg-Arg-Nal-Gly] | 23 | 743.39 | 744.7 |
| OD3 | cyc[D-Tyr-Arg-(Me)Arg-Nal-Gly] | 31 | 743.39 | 744.7 |
| OD5 | cyc[D-Tyr-Arg-Arg-(Me)Nal-Gly] | 894* | 743.39 | 744.7 |
| OD7 | cyc[D-Tyr-Arg-Arg-Nal-(Me)Gly] | 136 | 743.39 | 744.6 |
| OD9 | cyc[(Me)D-Tyr-Arg-Arg-Nal-Gly] | 247 | 743.39 | 744.7 |

The structure of OD1 (cyc[D-Tyr-(Me)Arg-Arg-Nal-Gly]) is as follows:

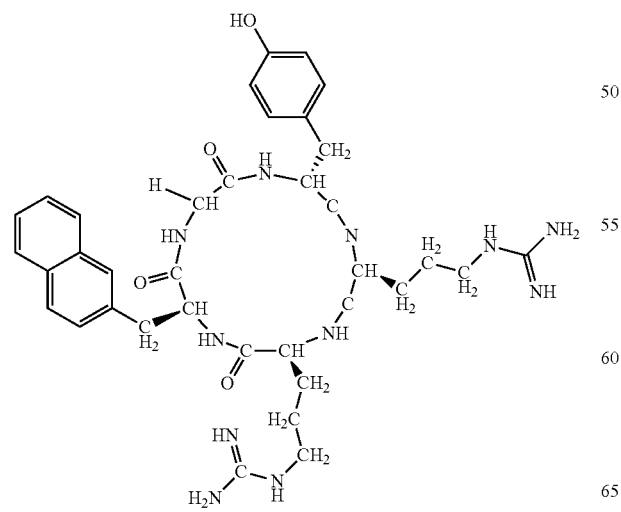

From these results, it can be observed that a loss of affinity by a factor of only 5-10 is obtained when Arg residues are methylated. A larger loss is obtained when other residues are methylated.

Corresponding results with $N^\alpha$-dimethylated pentapeptides are shown below (Table 2), indicating a further loss of affinity from such a modification:

TABLE 2

| Code | Sequence | IC$_{50}$ [nM] | Calculated mass | Observed m/z (m + H) |
|---|---|---|---|---|
| OD11 | cyc[(Me)Arg-Nal-Gly-(Me)D-Tyr-Arg] | >1000* | 757.4 | 758.7 |
| OD12 | cyc[(Me)Arg-(Me)Nal-Gly-D-Tyr-Arg] | >1000* | 757.4 | 758.6 |
| OD13 | cyc[Arg-Nal-(Me)Gly-(Me)D-Tyr-Arg] | >1000* | 757.4 | 758.7 |
| OD14 | cyc[Arg-(Me)Nal-Gly-(Me)D-Tyr-Arg] | >1000* | 757.4 | 758.6 |
| OD15 | cyc[Arg-Nal-(Me)Gly-D-Tyr-(Me)Arg] | ~300-400* | 757.4 | 758.8 |
| OD16 | cyc[Arg-Nal-Gly-(Me)D-Tyr-(Me)Arg] | ~1000* | 757.4 | 758.8 |
| OD18 | cyc[Arg-(Me)Nal-(Me)Gly-D-Tyr-Arg] | >1000* | 757.4 | 758.8 |
| OD19 | cyc[(Me)Arg-Nal-(Me)Gly-D-Tyr-Arg] | >1000* | 757.4 | 758.9 |
| OD20 | cyc[Arg-(Me)Nal-Gly-D-Tyr-(Me)Arg] | 100-200 | 757.4 | 758.7 |
| OD21 | cyc[(Me)Arg-Nal-Gly-D-Tyr-(Me)Arg] | >1000* | 757.4 | 758.6 |

The results of binding assays with pentapeptides in which Arg was substituted with ornithine or citrulline are shown in Table 3 below:

TABLE 3

| Code | Sequence | IC$_{50}$ [nM] | Calculated mass | Observed m/z (m + H) |
|---|---|---|---|---|
| OD23 | cyc[Nal-Gly-D-Tyr-Orn-Orn] | >1000* | 645.33 | 646.5 |
| OD24 | cyc[Nal-Gly-D-Tyr-Arg-Orn] | ~1000* | 687.35 | 688.6 |
| OD25 | cyc[Nal-Gly-D-Tyr-Orn-Arg] | 9 ± 0.1 | 687.35 | 688.4 |
| OD26 | cyc[Nal-Gly-D-Tyr-Cit-Cit] | >1000* | 731.34 | 732.6 |
| OD27 | cyc[Nal-Gly-D-Tyr-Cit-Arg] | 35 ± 7 | 730.36 | 731.6 |
| OD28 | cyc[Nal-Gly-D-Tyr-Arg-Cit] | >1000* | 730.36 | 731.7 |

The results of Table 3 indicate that the first Arg residue in cyclic pentapeptides may be substituted with a cationic residue, such as ornithine, without dramatic loss of affinity.

In an evaluation of side chain-acylated ornithine derivatives for incorporation of $^{18}$F-containing prosthetic groups, it was found that the fluorobenzoylated derivative showed the highest affinity (11 nM—see panel above). This compound showed a relatively high lipophilicity (Log P 1.06).

A number of other Orn-N$^δ$ and/or Orn-N$^α$-modified pentapeptides were also prepared, including a series of derivatives with N$^δ$ spacer moieties. The CXCR4 binding results are shown in Table 4.

TABLE 4

| Sequence | IC$_{50}$ [nM] | Calculated mass | Observed m/z (m + H) |
|---|---|---|---|
| cyc[D-Tyr-Orn(Me)-Arg-Nal-Gly] | 105 ± 7 | 701.36 | 702.7 |
| cyc[D-Tyr-Orn(Bz)-Arg-Nal-Gly] | 155 ± 63 | 777.4 | 778.6 |
| cyc[D-Tyr-Orn(N1)-Arg-Nal-Gly] | 40 ± 3 | 827.41 | 828.6 |
| cyc[D-Tyr-Orn(N2)-Arg-Nal-Gly] | 49 ± 1 | 827.41 | 828.7 |
| cyc[D-Tyr-Orn(Me,N1)-Arg-Nal-Gly] | 39.7 | 841.43 | 842.7 |
| cyc[D-Tyr-Orn(Me,N2)-Arg-Nal-Gly] | 34.2 | 841.43 | 842.7 |
| cyc[D-Tyr-Orn(FB)-Arg-Nal-Gly] | 11 ± 2 | 809.37 | 810.6 |
| cyc[D-Tyr-Orn(Bz,FB)-Arg-Nal-Gly] | 100 | 899.41 | 900.7 |
| cyc[D-Tyr-Orn(Me,FB)-Arg-Nal-Gly] | 78 ± 25 | 823.38 | 824.6 |

TABLE 4-continued

| Sequence | IC$_{50}$ [nM] | Calculated mass | Observed m/z (m + H) |
|---|---|---|---|
| cyc[D-Tyr-Orn(Ahx)-Arg-Nal-Gly] | 70 ± 23 | 800.43 | 801.7 |
| cyc[D-Tyr-Orn(Ahx$_2$)-Arg-Nal-Gly] | 947* | 913.51 | 914.9 |
| cyc[D-Tyr-Orn(Ahx$_3$)-Arg-Nal-Gly] | 227 | 1026.6 | 1027.9 |
| cyc[D-Tyr-Orn(TGAS)-Arg-Nal-Gly] | 125 | 832.42 | 833.7 |
| cyc[D-Tyr-Orn(TGAS$_2$)-Arg-Nal-Gly] | 189 | 977.49 | 978.9 |
| cyc[D-Tyr-Orn(TGAS$_3$)-Arg-Nal-Gly] | 146 | 1122.57 | 1123.9 |
| cyc[D-Tyr-Orn(Ac)-Arg-Nal-Gly] | 29 ± 11 | 729.36 | 730.6 |
| cyc[D-Tyr-Orn(Am)-Arg-Nal-Gly] | 35 ± 7 | 730.36 | 731.6 |
| cyc[D-Tyr-Orn(FP)-Arg-Nal-Gly] | 35 ± 13 | 761.37 | 762.6 |
| cyc[D-Tyr-Orn(Palm)-Arg-Nal-Gly] | >1000* | 925.58 | 926.9 |

In addition, a series of pentapeptides containing derivatives of D-Orn were prepared, together with pentapeptides in which B is His or Phe. The CXCR4-binding results are shown in Table 5.

TABLE 5

| Sequence | IC$_{50}$ [nM] | Calculated mass | Observed m/z (m + H) |
|---|---|---|---|
| cyc[D-Tyr-D-Orn(FB)-Arg-Nal-Gly] | 86 | 809.37 | 810.6 |
| cyc[D-Tyr-(Me)D-Orn(FB)-Arg-Nal-Gly] | 8.7 ± 0.6 | 823.38 | 824.6 |
| cyc[D-Tyr-(Me)D-Orn(Me,FB)-Arg-Nal-Gly] | 59 | 837.4 | 838.6 |
| cyc[D-Tyr-His-Arg-Nal-Gly] | 30 | | |
| cyc[D-Tyr-Phe-Arg-Nal-Gly] | 154 | | |

A number of cyclic hexapeptides in which an Ala or similar residue was inserted in the chain were tested for binding affinity to CXCR4. The results are shown in Table 6 (note—Dap(FP) is (N-fluoropropionyl)-diaminopropionic acid):

TABLE 6

| Code | Sequence | IC$_{50}$ [nM] |
|---|---|---|
| CPCR4* | cyc[D-Tyr-Arg-Arg-Nal-Gly] | 4 |
| BL 36 | cyc[D-Tyr-Arg-Arg-Nal-Ala-Gly] | 75 (±7) |
| BL 56 | cyc[D-Tyr-Arg-Arg-Nal-D-Ala-Gly] | >1000* |
| BL 58 | cyc[D-Tyr-Arg-Arg-Nal-Dap(FP)-Gly] | ~1000* |
| BL 37 | cyc[D-Tyr-Arg-Arg-D-Ala-Nal-Gly] | ~1000* |
| BL 38 | cyc[D-Tyr-Arg-Arg-nal-Nal-Gly] | >1000* |
| BL 39 | cyc[D-Tyr-Arg-Arg-D-Ala-Ala-Gly] | >1000* |
| BL 40 | cyc[D-Tyr-Arg-Arg-nal-Ala-Gly] | ~1000* |
| BL 42 | cyc[D-Tyr-Arg-Arg-Nal-Nal-Gly] | >1000* |
| BL130 | cyc[D-Tyr-Arg-Arg-Nal-Gly-Gly] | ~1000* |
| BL131 | cyc[D-Tyr-Arg-Arg-Ala-Nal-Gly] | >1000* |
| BL132 | cyc[D-Tyr-Arg-Ala-Arg-Nal-Gly] | >1000* |
| BL133 | cyc[D-Tyr-Arg-D-Ala-Arg-Nal-Gly] | >1000* |
| BL134 | cyc[D-Tyr-D-Ala-Arg-Arg-Nal-Gly] | >1000* |
| BL135 | cyc[D-Tyr-Ala-Arg-Arg-Nal-Gly] | >1000* |
| BL136 | cyc[D-Ala-D-Tyr-Arg-Arg-Nal-Gly] | >1000* |
| BL137 | cyc[Ala-D-Tyr-Arg-Arg-Nal-Gly] | ~1000* |
| BL158 | cyc[D-Tyr-Arg-Arg-Nal-Ala-Ala] | 114 |

The results of Table 6 suggest that Ala may be inserted between Nal and Gly, and/or Gly may be replaced with Ala, with only moderate loss of affinity. Insertion of other residues in this position, or insertion of any of the residues studied in Table 6 in other positions, was not well tolerated.

A further N$^\alpha$-methyl scan was conducted with a series of cyclic hexapeptides (N-mono-, di- and trimethylated), as reported in Table 7:

TABLE 7

| Code | Sequence | IC$_{50}$ [nM] |
| --- | --- | --- |
| BL56 | cyc[Arg-Nal-D-Ala-Gly-D-Tyr-Arg] | >1000* |
| BL58 | cyc[Arg-Nal-Dap(FP)-Gly-D-Tyr-Arg] | ~1000* |
| BL66 | cyc[(Me)Arg-Nal-Ala-Gly-D-Tyr-Arg] | >1000* |
| BL67 | cyc[Arg-(Me)Nal-Ala-Gly-D-Tyr-Arg] | >1000* |
| BL68 | cyc[Arg-Nal-(Me)Ala-Gly-D-Tyr-Arg] | >1000* |
| BL69 | cyc[Arg-Nal-Ala-(Me)Gly-D-Tyr-Arg] | >1000* |
| BL70 | cyc[Arg-Nal-Ala-Gly-(Me)D-Tyr-Arg] | ~200-300 |
| BL71 | cyc[Arg-Nal-Ala-Gly-D-Tyr-(Me)Arg] | ~1000* |
| BL72 | cyc[(Me)Arg-Nal-Ala-Gly-D-Tyr-(Me)Arg] | >1000* |
| BL73 | cyc[Arg-(Me)Nal-Ala-Gly-D-Tyr-(Me)Arg] | >1000* |
| BL74 | cyc[Arg-Nal-(Me)Ala-Gly-D-Tyr-(Me)Arg] | >1000* |
| BL75 | cyc[Arg-Nal-Ala-(Me)Gly-D-Tyr-(Me)Arg] | >1000* |
| BL76 | cyc[Arg-Nal-Ala-Gly-(Me)D-Tyr-(Me)Arg] | >1000* |
| BL77 | cyc[(Me)Arg-Nal-Ala-Gly-(Me)D-Tyr-Arg] | >1000* |
| BL78 | cyc[Arg-(Me)Nal-Ala-Gly-(Me)D-Tyr-Arg] | >1000* |
| BL79 | cyc[Arg-Nal-(Me)Ala-Gly-(Me)D-Tyr-Arg] | >1000* |
| BL80 | cyc[Arg-Nal-Ala-(Me)Gly-(Me)D-Tyr-Arg] | >1000* |
| BL81 | cyc[(Me)Arg-Nal-Ala-(Me)Gly-D-Tyr-Arg] | >1000* |
| BL82 | cyc[Arg-(Me)Nal-Ala-(Me)Gly-D-Tyr-Arg] | >1000* |
| BL83 | cyc[Arg-Nal-(Me)Ala-(Me)Gly-D-Tyr-Arg] | >1000* |
| BL84 | cyc[(Me)Arg-Nal-(Me)Ala-Gly-D-Tyr-Arg] | >1000* |
| BL85 | cyc[Arg-(Me)Nal-(Me)Ala-Gly-D-Tyr-Arg] | >1000* |
| BL86 | cyc[(Me)Arg-(Me)Nal-Ala-Gly-D-Tyr-Arg] | >1000* |
| BL88 | cyc[Arg-Nal-(Me)Ala-Gly-(Me)D-Tyr-(Me)Arg] | >1000* |
| BL89 | cyc[Arg-(Me)Nal-Ala-Gly-(Me)D-Tyr-(Me)Arg] | >1000* |
| BL92 | cyc[Arg-(Me)Nal-Ala-(Me)Gly-D-Tyr-(Me)Arg] | >1000* |
| BL93 | cyc[(Me)Arg-Nal-Ala-(Me)Gly-D-Tyr-(Me)Arg] | >1000* |
| BL94 | cyc[Arg-(Me)Nal-(Me)Ala-Gly-D-Tyr-(Me)Arg] | >1000* |
| BL96 | cyc[Arg-Nal-(Me)Ala-(Me)Gly-(Me)D-Tyr-Arg] | >1000* |
| BL97 | cyc[Arg-(Me)Nal-Ala-(Me)Gly-(Me)D-Tyr-Arg] | >1000* |
| BL98 | cyc[(Me)Arg-Nal-Ala-(Me)Gly-(Me)D-Tyr-Arg] | >1000* |
| BL99 | cyc[Arg-(Me)Nal-(Me)Ala-Gly-(Me)D-Tyr-Arg] | >1000* |
| BL102 | cyc[Arg-(Me)Nal-(Me)Ala-(Me)Gly-D-Tyr-Arg] | >1000* |
| BL104 | cyc[(Me)Arg-(Me)Nal-Ala-(Me)Gly-D-Tyr-Arg] | >1000* |

These results indicate appreciable loss of binding affinity after N$^\alpha$-methylation of cyclic hexapeptides, although the N-methyl-D-Tyr hexapeptide did not suffer such a significant loss of affinity as most of the other derivatives.

In order to allow more flexibility for the attachment of prosthetic groups for labeling, the introduction of an amino group was investigated by substitution of the Gly residue in CPCR4 for Dap. The results (Table 8) indicate only a moderate loss of affinity following this substitution (note—FP: 2-fluoropropionyl; FB: 4-fluorobenzoyl).

TABLE 8

| Code | Sequence | $IC_{50}$ [nM] |
|---|---|---|
| CPCR4 | cyc[D-Tyr-Arg-Arg-Nal-Gly] | 4 |
| Dap(FP)-8k | cyc[D-Tyr-Arg-Arg-Nal-Dap(FP)] | 140 |
| Dap(FB)-8k | cyc[D-Tyr-Arg-Arg-Nal-Dap(FB)] | 350* |

Other possible modifications of CPCR4 or the other peptides described herein include Nal substitutions with other fluorine-containing aromatic moieties as analogues for the corresponding $^{18}$F-labeled compounds. For example:

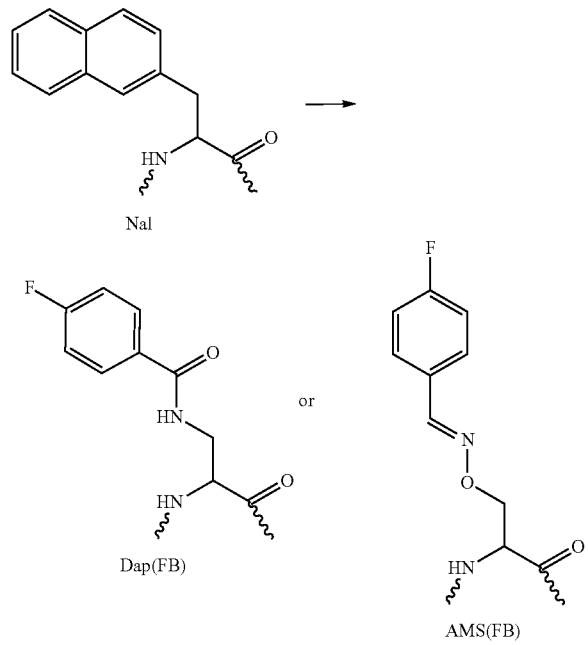

AMS(FB) is an oxime of an aminooxy-serine moiety and 4-fluorobenzaldehyde.

For the development of fluorescent CXCR4 ligands, it is possible to substitute Nal with a fluorescent Dap derivative, such as Dap(NBD) (NBD is 7-nitro-1,2,3-benzoxadiazole). This derivative showed an affinity which was reduced compared to CPCR4, although results from FACS analysis suggest that such a ligand may still be suitable for the investigation of CXCR4 expression by such a technique.

EXAMPLE 3

Multimodal Molecular Imaging of CXCR4 Chemokine Receptor Expression with Peptide-Based PET Probes and Bioluminescence A key role in metastasis and organ specific homing of tumor cells is attributed to the chemokine receptor CXCR4 and its endogenous ligand SDF-1α. For targeting of CXCR4 expression in vivo we developed a radiolabeled cyclic peptide, CPCR4. $^{125}$I-CPCR4 is the first PET imaging probe that binds with high affinity to CXCR4 ($K_D$=0.4 nM), shows high accumulation in CXCR4 expressing tumors in vivo (5.5% ID/g, 1 h post injection), and allows a clear delineation of CXCR4 positive tumors.

To allow correlation of tumor development with receptor expression and to monitor potential therapeutic interventions using the non-radiolabeled probe by multimodality (bioluminescence and nuclear) imaging, tumor cells have been transduced with luciferase (luc). Lentiviral vectors were constructed containing genes of CXCR4 and luc or otherwise only luc or eGFP as controls. These vectors were successfully used for stable transduction of murine CMS5 fibrosarcoma cells. Surface expression of CXCR4 on CMS5/CXCR4/luc cells was investigated in radioligand binding assays and FACS studies. High affinity and specificity of CPCR4-binding and functional expression of luc were ascertained in cell assays. Transduced cells were injected subcutaneously into nude mice. Animals were analyzed with μ-PET using radiolabeled CPCR4 and bioluminescence (luc)/fluorescence (eGFP) imaging. Ex vivo analysis was performed by autoradiography, bioluminescence measurements and immunohistochemistry. For a better understanding of CPCR4-binding and to design ligands with improved pharmacokinetics, a newly proposed CXCR4 receptor model has been developed and is currently validated by investigating CXCR4 receptor mutants. Based on this computer model, studies on the structure-activity relationship of CPCR4-derivatives are performed for tracer optimization and investigation of other labeling options.

In conclusion, this approach allows imaging of CXCR4 expression in vivo and allows development of enhanced imaging probes for the non-invasive investigation of the metastatic potential of tumors and determination of CXCR4 expression for individualized therapy.

EXAMPLE 4

Preparation of a Conjugate Between a CXCR4-Binding Cyclic Oligopeptide and a Chelating Agent The person of ordinary skill in the art would readily be able to prepare a construct or conjugate consisting of a cyclic oligopeptide of the present invention, a suitable spacer moiety (preferably one of the linker moieties described herein), and a chelator or other moiety suitable for complexation of a radiometal. Typically, as described in numerous publications in recent years, DOTA, for example, is coupled to a linker-bearing, fully protected oligopeptide, either using a tri-protected (e.g. tri-tert-butyl-protected) DOTA using standard activation procedures, or using pre-activated species of DOTA, for example mono-, di-, tri- or tetra N-succinimidyl esters or 4-nitrophenyl esters of DOTA. Alternatively, standard peptide coupling conditions can be used to achieve this goal.

Similarly, other chelators/complexation moieties, such as TETA or DTPA, can be coupled. DTPA may also be coupled using the cyclic bis-anhydride. Obviously, the chelator may also be pre-coupled to the spacer, thus resulting in the formation of the peptide-spacer bond in the final step.

This coupling can also be achieved by a person of ordinary skill in the art using the well-described coupling procedures established in the radiopharmaceutical field. Other coupling routes such as oxime or hydrazone formation, as well as other selective methods, such as the reaction of thiols and maleimides, may be used to reach similar results.

The foregoing Examples are intended to illustrate specific embodiments of the present invention and are not intended to limit the scope thereof, the scope being defined by the appended claims. All documents cited herein are incorporated herein by reference in their entirety.

REFERENCES

1. Fujii, N., et al., Molecular-size reduction of a potent CXCR4-chemokine antagonist using orthogonal combination of conformation- and sequence-based libraries. Angew Chem Int Ed Engl, 2003. 42(28): p. 3251-3.
2. Haubner, R., et al., Radiolabeled alpha(v)beta3 integrin antagonists: a new class of tracers for tumor targeting. J Nucl Med, 1999. 40(6): p. 1061-71.
3. Gansbacher, B., et al., Retroviral vector-mediated gamma-interferon gene transfer into tumor cells generates potent and long lasting antitumor immunity. Cancer Res, 1990. 50(24): p. 7820-5.
4. DuBridge, R. B., et al., Analysis of mutation in human cells by using an Epstein-Barr virus shuttle system. Mol Cell Biol, 1987. 7(1): p. 379-87.
5. Loetscher, M., et al., Cloning of a human seven-transmembrane domain receptor, LESTR, that is highly expressed in leukocytes. J Biol Chem, 1994. 269(1): p. 232-7.
6. Anton, M., et al., Use of the norepinepluine transporter as a reporter gene for non-invasive imaging of genetically modified cells. J Gene Med, 2004. 6(1): p. 119-26.
7. Fan, G. H., et al., Hsc/Hsp70 interacting protein (hip) associates with CXCR2 and regulates the receptor signaling and trafficking. J Biol Chem, 2002. 277(8): p. 6590-7.
8. Forster, R., et al., Intracellular and surface expression of the HIV-1 coreceptor CXCR4/fusin on various leukocyte subsets: rapid internalization and recycling upon activation. J Immunol, 1998. 160(3): p. 1522-31.
9. Gupta, S. K., et al., Pharmacological evidence for complex and multiple site interaction of CXCR4 with SDF-1alpha: implications for development of selective CXCR4 antagonists. Immunol Lett, 2001. 78(1): p. 29-34.
10. Hesselgesser, J., et al., Identification and characterization of the CXCR4 chemokine receptor in human T cell lines: ligand binding, biological activity, and HIV-1 infectivity. J Immunol, 1998. 160(2): p. 877-83.
11. Balkwill, F., Nature Reviews, 2004, 4: p. 540-550
12. Tamamura H et al., J Med Chem, 2005, 48: p. 3280-9
13. Fields G B, Noble R L. Solid phase peptide synthesis utilizing 9-fluorenylmethoxycarbonyl amino acids. Int. J. Pept. Protein Res. 1990; 35: p. 161-214.
14. Biron E, Chatteijee J, Kessler H. Optimized Selective N-Methylation of Peptides on Solid Support. J. Peptide Sci. 2006; 12: p. 213-219.

---

The invention claimed is:

1. A compound or conjugate, or a pharmaceutically acceptable salt or ester thereof, comprising a ligand for the chemokine receptor CXCR4 and a detectable label, the ligand having a binding affinity for the CXCR4 receptor, measured as $IC_{50}$ in the presence of $^{125}I$-CPCR4, of 250 nM or lower, wherein the ligand comprises a cyclic oligopeptide moiety, wherein the cyclic oligopeptide moiety is:

cyclo[D-Tyr/(Me)D-Tyr-B-Arg/(Me)Arg-Z-(Ala)$_n$-X]

wherein:
B is selected from the group consisting of substituted Arg, substituted Orn, Cit or substituted Cit, His or substituted His, Phe or substituted Phe, Lys or substituted Lys, 2,3-diaminopropionic acid (Dap) or substituted Dap, and 2,4-diaminobutyric acid (Dab) or substituted Dab; provided that if B is substituted with methyl, it is followed by Arg;
Z is an amino acid containing an aromatic group in its side chain;
X is selected from the group consisting of Ala or substituted Ala, Gly or substituted Gly, and Dap or substituted Dap;
n is 1 or 0, provided that n is 1 only when B is Arg and Z is L-3-(2-naphthyl)alanine (Nal).

2. A compound or conjugate according to claim 1 wherein Z is selected from the group consisting of Nal, (N-fluoropropionyl)-diaminopropionic acid (Dap(FB)) and an oxime of aminooxy serine and 4-flurobenzaldehvde (AMS(FB)).

3. A compound or conjugate according to claim 1 wherein B is $N^\alpha$-substituted with a Me group.

4. A compound or conjugate according to claim 1 wherein B is substituted Orn, the ornithine residue is substituted at $N^\delta$ with one or two groups selected from fluorobenzoyl (FB), fluoropropionyl (FP), acetyl (Ac), amido (Am), Me, 1-naphthylmethyl (N1), 2-naphthylmethyl (N2), benzyl (Bz) and acyl spacer moieties, wherein the acyl spacer moiety is an acyl group containing a chain of 1-14 carbons, optionally interrupted by heteroatoms, and having a nucleophilic functional group at its end distal to the ornithine $N^\delta$; or the ornithine residue is substituted at $N^\alpha$ with a Me group.

5. A compound or conjugate according to claim 4 wherein the acyl spacer moiety is selected from aminohexanoyl (Ahx), triethyleneglycolamino acyl (TGAS), (Ahx)$_2$, (Ahx)$_3$, (TGAS)$_2$ and (TGAS)$_3$.

6. A compound or conjugate according to claim 1 wherein B is Orn substituted at $N^\delta$ with FB, FP, Ac, Am, N1, N2, Me and N1, Me and N2, Bz, Bz and FB, Bz and FP, Me and FB, Me and FP, and optionally substituted at $N^\alpha$ or $N^\delta$ with a Me group.

7. A compound or conjugate according to claim 1, wherein the cyclic oligopeptide moiety has the sequence: cyclo[D-Tyr-B-Arg-Z-X], wherein B, Z and X are as defined in claim 2, provided that not more than one of the residues in the said sequence is $N^\alpha$-methylated.

8. A compound or conjugate according to claim 1, wherein B is selected from Arg, (Me)Arg, Orn, Cit, Orn(FB), Orn(FP), Orn(Ac), Orn(Am), Orn(N1), Orn(N2), Orn(Me, N1), Orn (Me, N2), Orn(Me), Orn(Bz), Orn(Bz,FB), Orn(Ahx), Orn (Ahx$_2$), Orn(Ahx$_3$), Orn(TGAS), Orn(TGAS$_2$), Orn (TGAS$_3$), Orn(Me, FB), D-Orn(FB), (Me)D-Orn(FB), (Me)D-Orn(Me,FB), His and Phe, provided that not more than one of the residues in the said sequence is $N^\alpha$-methylated.

9. A compound or conjugate according to claim 1, wherein the first residue is D-Tyr, the third residue is Arg, Z is Nal, and X is Gly.

10. A compound or conjugate according to claim 1, wherein the cyclic oligopeptide moiety has a sequence selected from the group consisting of

```
cyclo[D-Tyr-(Me)Arg-Arg-Nal-Gly]
cyclo[D-Tyr-Arg-(Me)Arg-Nal-Gly]
cyclo[D-Tyr-Arg-Arg-Nal-(Me)Gly]
cyclo[D-Tyr-Cit-Arg-Nal-Gly]
cyclo[D-Tyr-Arg-Arg-Nal-Ala-Gly]
cyclo[D-Tyr-Arg-Arg-Nal-Ala-Ala]
cyclo[D-Tyr-(Me)Arg-Arg-Nal-(Me)Gly]
cyclo[D-Tyr-(Me)Arg-Arg-(Me)Nal-Gly]
cyclo[(Me)D-Tyr-Arg-Arg-Nal-Ala-Gly]
cyclo[(Me)D-Tyr-Arg-Arg-Nal-Gly]
cyclo[D-Tyr-Orn(FB)-Arg-Nal-Gly]
cyclo[D-Tyr-Orn(FP)-Arg-Nal-Gly]
cyclo[D-Tyr-Orn(Ac)-Arg-Nal-Gly]
cyclo[D-Tyr-Orn(Am)-Arg-Nal-Gly]
cyclo[D-Tyr-Arg-Arg-Nal-Dap(FP)]
cyclo[D-Tyr-Orn(N1)-Arg-Nal-Gly]
cyclo[D-Tyr-Orn(N2)-Arg-Nal-Gly]
cyclo[D-Tyr-Orn(Me,N1)-Arg-Nal-Gly]
cyclo[D-Tyr-Orn(Me,N2)-Arg-Nal-Gly]
cyclo[D-Tyr-Orn(Me)-Arg-Nal-Gly]
cyclo[D-Tyr-Orn(Bz)-Arg-Nal-Gly]
cyclo[D-Tyr-Orn(Bz,FB)-Arg-Nal-Gly]
cyclo[D-Tyr-Orn(Ahx)-Arg-Nal-Gly]
cyclo[D-Tyr-Orn(Ahx₃)-Arg-Nal-Gly]
cyclo[D-Tyr-Orn(TGAS)-Arg-Nal-Gly]
cyclo[D-Tyr-Orn(TGAS₂)-Arg-Nal-Gly]
cyclo[D-Tyr-Orn(TGAS₃)-Arg-Nal-Gly]
cyclo[D-Tyr-Orn(Me,FB)-Arg-Nal-Gly]
cyclo[D-Tyr-D-Orn(FB)-Arg-Nal-Gly]
cyclo[D-Tyr-(Me)D-Orn(FB)-Arg-Nal-Gly]
cyclo[D-Tyr-(Me)D-Orn(Me,FB)-Arg-Nal-Gly]
cyclo[D-Tyr-His-Arg-Nal-Gly]
and
cyclo[D-Tyr-Phe-Arg-Nal-Gly].
```

11. A compound or conjugate according to claim 10, wherein the cyclic oligopeptide moiety has a sequence selected from the group consisting of

```
cyclo[D-Tyr-(Me)Arg-Arg-Nal-Gly]
cyclo[D-Tyr-Arg-(Me)Arg-Nal-Gly]
cyclo[D-Tyr-Cit-Arg-Nal-Gly]
cyclo[D-Tyr-Orn(FB)-Arg-Nal-Gly]
cyclo[D-Tyr-Orn(FP)-Arg-Nal-Gly]
cyclo[D-Tyr-Orn(Ac)-Arg-Nal-Gly]
cyclo[D-Tyr-Orn(Am)-Arg-Nal-Gly]
cyclo[D-Tyr-Orn(N1)-Arg-Nal-Gly]
cyclo[D-Tyr-Orn(N2)-Arg-Nal-Gly]
cyclo[D-Tyr-Orn(Me,N1)-Arg-Nal-Gly]
cyclo[D-Tyr-Orn(Me,N2)-Arg-Nal-Gly]
cyclo[D-Tyr-(Me)D-Orn(FB)-Arg-Nal-Gly],
and
cyclo[D-Tyr-His-Arg-Nal-Gly].
```

12. A compound or conjugate according to claim 11 wherein the cyclic oligopeptide moiety has a sequence selected from

```
cyclo[D-Tyr-Orn(FB)-Arg-Nal-Gly]
or
cyclo[D-Tyr-(Me)D-Orn(FB)-Arg-Nal-Gly].
```

13. A compound or conjugate according to claim 1, wherein the label is a radiolabel selected from $^{18}$F, $^{47}$Sc, $^{51}$Cr, $^{52}$Fe, $^{52m}$Mn, $^{56}$Ni, $^{57}$Ni, $^{62}$Cu, $^{64}$Cu, $^{67}$Ga, $^{68}$Ga, $^{72}$As, $^{75}$Br, $^{76}$Br, $^{77}$Br, $^{82}$Br, $^{89}$Zr, $^{94m}$Tc, $^{97}$Ru, $^{99m}$Tc, $^{111}$In, $^{123}$I, $^{124}$I, $^{125}$I, $^{131}$I, $^{191}$Pt, $^{197}$Hg, $^{201}$Tl, $^{203}$Pb, $^{110m}$In, $^{120}$I.

14. A compound or conjugate according to claim 1 wherein the compound has a $^{18}$F label present on an FB or FP substituent at $N^\delta$ of Orn or D-Orn.

15. A compound or conjugate according to claim 1 wherein the conjugate has a radiolabel which is attached to the ligand by conjugation of an organic complexation agent and a radionuclide.

16. A compound or conjugate according to claim 15, wherein the complexation agent is attached to the ligand through a spacer group.

17. A compound or conjugate according to claim 1, wherein the label is a radiolabel selected from the group consisting of $^{32}$P, $^{67}$Cu, $^{77}$As, $^{90}$Y, $^{99}$Mo, $^{103}$Ru, $^{105}$Rh, $^{109}$Pd, $^{111}$Ag, $^{114m}$In, $^{117m}$Sn, $^{121}$Sn, $^{127}$Te, $^{131}$I, $^{140}$La, $^{140}$Nd, $^{142}$Pr, $^{143}$Pr, $^{149}$Tb, $^{149}$Pm, $^{151}$Pm, $^{153}$Sm, $^{159}$Gd, $^{161}$Tb, $^{166}$Ho, $^{166}$Dy, $^{169}$Er, $^{169}$Yb, $^{172}$Tm, $^{175}$Yb, $^{177}$Lu, $^{186}$Re, $^{188}$Re, $^{198}$Au, $^{199}$Au, $^{211}$At, $^{211}$Bi, $^{212}$Bi, $^{213}$Bi, $^{225}$Ac.

18. A method of imaging neoplastic tissue, the method comprising administering to a subject having or suspected of having a neoplasia, a compound or conjugate of claim 1, and detecting the compound following distribution thereof in vivo by imaging the subject.

19. A method according to claim 18 wherein the imaging is performed using PET or SPECT when the label is a radionuclide.

* * * * *

UNITED STATES PATENT AND TRADEMARK OFFICE
CERTIFICATE OF CORRECTION

PATENT NO. : 8,628,750 B2
APPLICATION NO. : 12/280829
DATED : January 14, 2014
INVENTOR(S) : Hans Jurgen Wester et al.

It is certified that error appears in the above-identified patent and that said Letters Patent is hereby corrected as shown below:

In the Claims

Column 87, lines 54 and 55 "B is selected from the group consisting of substituted Arg, substituted Orn, Cit or substituted Cit, His or substituted" should be -- B is selected from the group consisting of Arg or substituted Arg, Orn or substituted Orn, Cit or substituted Cit, His or substituted --.

Signed and Sealed this
Twenty-ninth Day of April, 2014

Michelle K. Lee
*Deputy Director of the United States Patent and Trademark Office*